(12) United States Patent
Suenaga et al.

(10) Patent No.: US 11,096,883 B2
(45) Date of Patent: Aug. 24, 2021

(54) COMPOSITION, ARTIFICIAL NAIL COMPOSITION, NAIL DECORATION MATERIAL, ARTIFICIAL NAIL, STORED CONTAINER, IMAGE FORMING APPARATUS, AND IMAGE FORMING METHOD

(71) Applicant: RICOH COMPANY, LTD., Tokyo (JP)

(72) Inventors: Takenori Suenaga, Kanagawa (JP); Masahide Kobayashi, Kanagawa (JP); Mitsunobu Morita, Shizuoka (JP); Takashi Okada, Kanagawa (JP); Soh Noguchi, Kanagawa (JP); Tatsuki Yamaguchi, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 16/441,773

(22) Filed: Jun. 14, 2019

(65) Prior Publication Data

US 2020/0038309 A1 Feb. 6, 2020

(30) Foreign Application Priority Data

Jul. 31, 2018 (JP) .............................. JP2018-143434
Jan. 18, 2019 (JP) .............................. JP2019-006526

(51) Int. Cl.
*A61K 8/87* (2006.01)
*A61Q 3/02* (2006.01)

(52) U.S. Cl.
CPC . *A61K 8/87* (2013.01); *A61Q 3/02* (2013.01)

(58) Field of Classification Search
CPC .......... A61Q 3/02; A45D 31/00; A45D 44/00; A61K 8/87
See application file for complete search history.

(56) References Cited

U.S. PATENT DOCUMENTS

| | | | |
|---|---|---|---|
| 9,267,043 B2 | 2/2016 | Morita et al. | |
| 9,796,862 B2 | 10/2017 | Morita et al. | |
| 10,174,215 B2 | 1/2019 | Morita et al. | |
| 2013/0144057 A1 | 6/2013 | Morita | |
| 2014/0363634 A1* | 12/2014 | Morita | C09D 11/101 428/195.1 |
| 2015/0352032 A1* | 12/2015 | Abe | A61K 8/34 132/200 |
| 2016/0023984 A1 | 1/2016 | Morita et al. | |
| 2016/0075894 A1 | 3/2016 | Noguchi et al. | |
| 2017/0137644 A1 | 5/2017 | Morita et al. | |
| 2017/0209351 A1 | 7/2017 | Takemoto | |
| 2017/0312201 A1 | 11/2017 | Takemoto | |
| 2017/0319461 A1 | 11/2017 | Chen et al. | |
| 2018/0127607 A1* | 5/2018 | Morita | C09D 11/30 |

FOREIGN PATENT DOCUMENTS

| | | |
|---|---|---|
| JP | 4981184 | 4/2012 |
| JP | 5475067 | 2/2014 |
| JP | 2015-013980 | 1/2015 |
| JP | 2016-023144 | 2/2016 |
| JP | 2017-203023 | 11/2017 |
| JP | 2017-210456 | 11/2017 |
| JP | 2017-210475 | 11/2017 |
| JP | 2018-080321 | 5/2018 |
| JP | 6340243 | 5/2018 |
| WO | WO2016/072353 A1 | 5/2016 |

* cited by examiner

*Primary Examiner* — Blessing M Fubara
(74) *Attorney, Agent, or Firm* — Grüneberg and Myers PLLC

(57) ABSTRACT

Provided is a composition including: an acrylamide compound represented by general formula (1) in 20% by mass or greater but 50% by mass or less; a multifunctional monomer in 40% by mass or greater but 70% by mass or less; and a polymerization initiator,

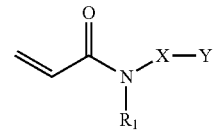

General formula (1)

where in general formula (1), $R_1$ represents alkyl group containing 1 through 6 carbon atoms, X represents alkylene group containing 1 through 6 carbon atoms, and Y represents any one selected from the group consisting of general formula (2) below and general formula (3) below,

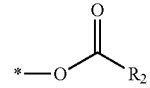

General formula (2)

where in general formula (2), $R_2$ represents alkyl group containing 1 through 10 carbon atoms, and * represents binding site with X above,

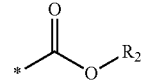

General formula (3)

where in general formula (3), $R_2$ represents alkyl group containing 1 through 10 carbon atoms, and * represents binding site with X above.

12 Claims, 2 Drawing Sheets

COMPOSITION, ARTIFICIAL NAIL COMPOSITION, NAIL DECORATION MATERIAL, ARTIFICIAL NAIL, STORED CONTAINER, IMAGE FORMING APPARATUS, AND IMAGE FORMING METHOD

CROSS-REFERENCE TO RELATED APPLICATIONS

The present application claims priority under 35 U.S.C. § 119 to Japanese Patent Application No. 2018-143434 filed Jul. 31, 2018 and Japanese Patent Application No. 2019-006526 filed Jan. 18, 2019. The contents of which are incorporated herein by reference in their entirety.

BACKGROUND OF THE INVENTION

Field of the Invention

The present disclosure relates to a composition, an artificial nail composition, a nail decoration material, an artificial nail, a stored container, an image forming apparatus, and an image forming method.

Description of the Related Art

Gel nail has been known as a nail decorating method. Gel nail is a nail material that has fluidity and photopolymerization reactivity of curing when irradiated with ultraviolet rays or visible light. Gel nail is often used in a three-stage structure including base gel, color gel, and top coat gel.

Top coat gel is used for coating color gel in order to impart gloss and a good durability. For example, there has been proposed a top coat composition containing a (meth)acrylic oligomer, a trifunctional (meth)acrylic monomer, and a polymerization initiator (for example, see International Publication No. WO 2016/072353).

There has also been proposed an artificial nail composition containing an acrylic functional group-containing compound having a specific structure (for example, see Japanese Unexamined Patent Application Publication No. 2016-23144).

There has also been proposed an artificial nail composition containing a tertiary amine acrylic resin or a thiol resin as a surface curing accelerator (for example, see Japanese Unexamined Patent Application Publication No. 2017-203023).

SUMMARY OF THE INVENTION

According to one aspect of the present disclosure, a composition contains an acrylamide compound represented by general formula (1) below in an amount of 20% by mass or greater but 50% by mass or less, a multifunctional monomer in an amount of 40% by mass or greater but 70% by mass or less, and a polymerization initiator.

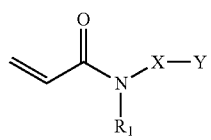

General formula (1)

In general formula (1), $R_1$ represents an alkyl group containing 1 through 6 carbon atoms, X represents an alkylene group containing 1 through 6 carbon atoms, and Y represents any one selected from the group consisting of general formula (2) below and general formula (3) below.

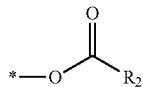

General formula (2)

In general formula (2), $R_2$ represents an alkyl group containing 1 through 10 carbon atoms, and * represents the binding site with X mentioned above.

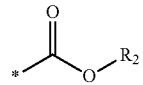

General formula (3)

In general formula (3), $R_2$ represents an alkyl group containing 1 through 10 carbon atoms, and * represents the binding site with X mentioned above.

DESCRIPTION OF THE EMBODIMENTS (Composition)

Figure 1:
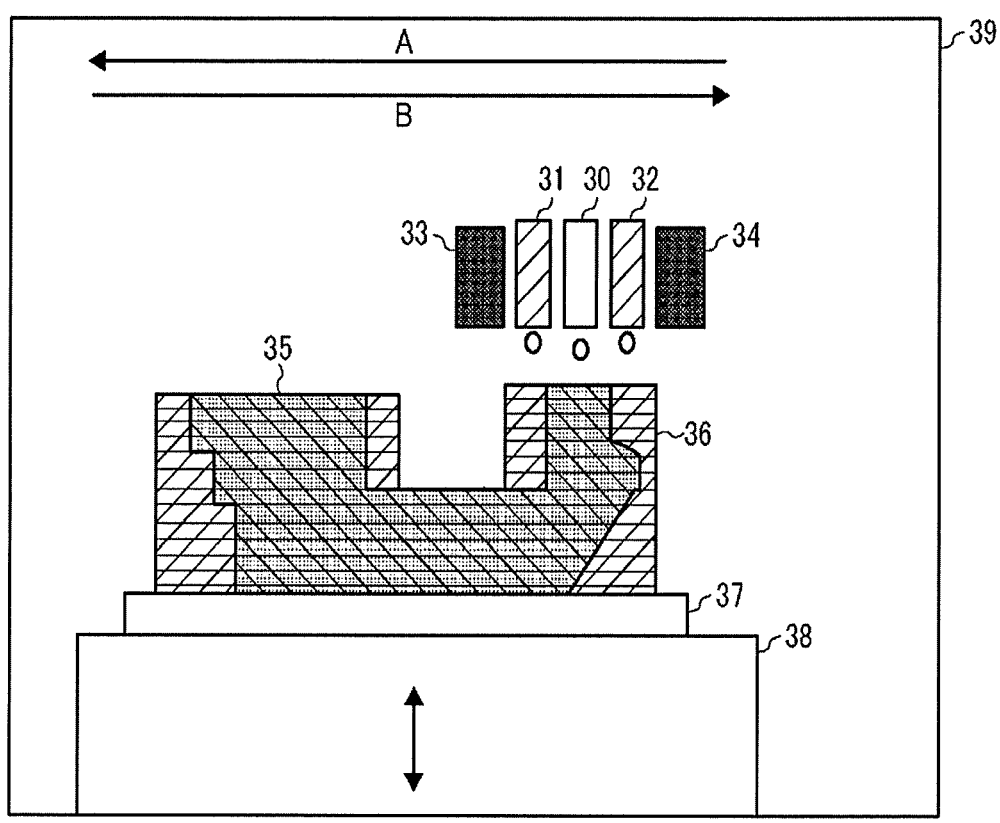
FIG. 1 is a schematic view illustrating an example of an image forming apparatus (three-dimensional stereoscopic image forming apparatus)
Figure 2A:
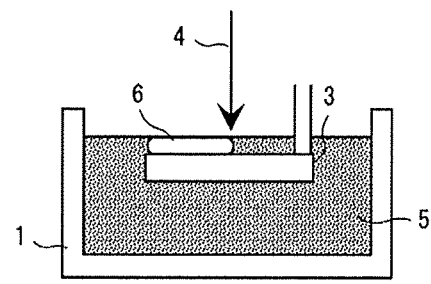
FIG. 2A is a schematic view illustrating an example of a method for forming a three-dimensional object using a composition.
Figure 2B:
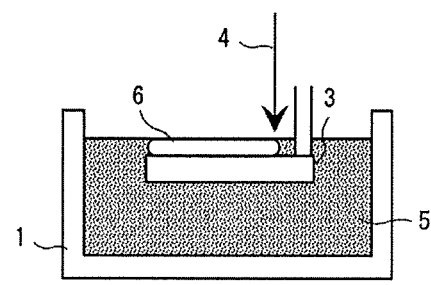
FIG. 2B is a schematic view illustrating an example of a method for forming a three-dimensional object using a composition.
Figure 2C:
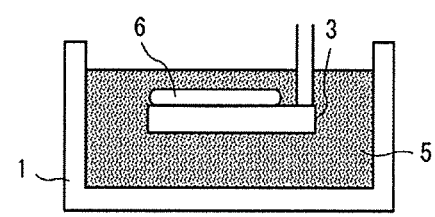
FIG. 2C is a schematic view illustrating an example of a method for forming a three-dimensional object using a composition.
Figure 2D:
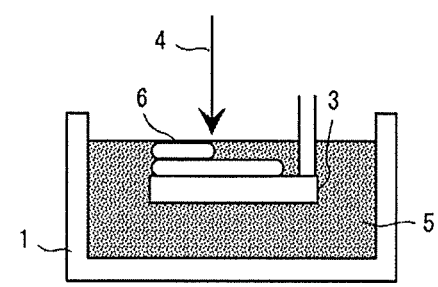
FIG. 2D is a schematic view illustrating an example of a method for forming a three-dimensional object using a composition.

A composition of the present disclosure contains an acrylamide compound represented by general formula (1) below in an amount of 20% by mass or greater but 50% by mass or less, a multifunctional monomer in an amount of 40% by mass or greater but 70% by mass or less, and a polymerization initiator, and further contains other components as needed.

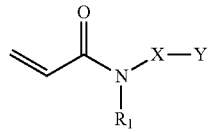

General formula (1)

In general formula (1), $R_1$ represents an alkyl group containing 1 through 6 carbon atoms, X represents an alkylene group containing 1 through 6 carbon atoms, and Y represents any one selected from the group consisting of general formula (2) below and general formula (3) below.

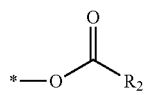

General formula (2)

In general formula (2), $R_2$ represents an alkyl group containing 1 through 10 carbon atoms, and * represents the binding site with X mentioned above.

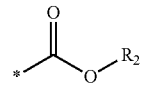

General formula (3)

In general formula (3), $R_2$ represents an alkyl group containing 1 through 10 carbon atoms, and * represents the binding site with X mentioned above.

The present disclosure has an object to provide a composition that can be reduced in odor and can provide a cured product excellent in curability and durability.

The present disclosure can provide a composition that can be reduced in odor and can provide a cured product excellent in curability and durability.

It is desired to avoid using the existing technique described in International Publication No. WO 2016/072353, because oxygen inhibition makes a curing reaction over the surface insufficient to make the process of wiping off any uncured monomer bothersome, or brings about a risk of any uncured monomer adhering to skin.

Moreover, the existing techniques described in Japanese Unexamined Patent Application Publication Nos. 2016-23144 and 2017-203023 do not satisfy odor reduction during use of the composition, and curability and durability of a cured product.

The composition of the present disclosure contains an acrylamide compound represented by general formula (1) above in an amount of 20% by mass or greater but 50% by mass or less, a multifunctional monomer in an amount of 40% by mass or greater but 70% by mass or less, and a polymerization initiator. Therefore, the composition is suitable as an artificial nail composition and can provide a cured product satisfying odor reduction and excellent in curability and durability.

The composition of the present disclosure is preferably a curable composition. Examples of the curable composition include a thermosetting composition and an active-energy-ray-curable composition. An active-energy-ray-curable composition is more preferable.

As used herein, (meth)acrylic acid ester refers to acrylic acid ester or methacrylic acid ester, and (meth)acrylate refers to acrylate or methacrylate.

<Acrylamide Compound>

The acrylamide compound is represented by general formula (1) above.

$R_1$ in general formula (1) represents a straight-chain or branched alkyl group containing 1 through 6 carbon atoms.

Examples of the alkyl group containing 1 through 6 carbon atoms include a methyl group, an ethyl group, a propyl group, an isopropyl group, an n-butyl group, an s-butyl group, an isobutyl group, a t-butyl group, a pentyl group, a neopentyl group, and a hexyl group.

X in general formula (1) represents a straight-chain or branched alkylene group containing 1 through 6 carbon atoms.

Examples of the alkylene group containing 1 through 6 carbon atoms include a methylene group, an ethylene group, a propylene group, and a butylene group.

Y in general formula (1) represents any one selected from the group consisting of general formula (2) above and general formula (3) above.

$R_2$ in general formula (2) above represents a straight-chain or branched alkyl group containing 1 through 10 carbon atoms.

Examples of the alkyl group containing 1 through 10 carbon atoms include a methyl group, an ethyl group, a propyl group, an isopropyl group, an n-butyl group, an s-butyl group, an isobutyl group, a t-butyl group, a pentyl group, a neopentyl group, a hexyl group, a heptyl group, an octyl group, a nonyl group, and a decyl group.

The "*" symbol in general formula (2) represents the binding site with X mentioned above.

$R_2$ in general formula (3) above represents a straight-chain or branched alkyl group containing 1 through 10 carbon atoms.

Examples of the alkyl group containing 1 through 10 carbon atoms include a methyl group, an ethyl group, a propyl group, an isopropyl group, an n-butyl group, an s-butyl group, an isobutyl group, a t-butyl group, a pentyl group, a neopentyl group, a hexyl group, a heptyl group, an octyl group, a nonyl group, and a decyl group.

The "*" symbol in general formula (3) represents the binding site with X mentioned above.

It is preferable that Y in general formula (1) representing the acrylamide compound having an ester structure be represented by general formula (3) above.

It is preferable that $R_2$ in general formula (3) above be an alkyl group containing 1 through 2 carbon atoms.

The acrylamide compound represented by general formula (1) is a monofunctional acyclic tertiary acrylamide having an ester structure at an end. Typically, low-molecular-weight tertiary acrylamide compounds have volatility and hence a strong odor unique to monomers, leading to discomfort during handling of compositions containing these compounds.

Hence, the tertiary acrylamide compound represented by general formula (1) above has an ester structure at an end. Hence, volatility reduction owing to the ester structure enables odor suppression. Moreover, it is considered that intermolecular interaction owing to the presence of the ester structure can improve curability.

There are many commercially available products of acrylamide compounds containing a polymerizable acrylamide group but free of an ester structure (e.g., N-acryloylmorpholine, N,N-dimethyl acrylamide, N,N-diethyl acrylamide, N-isopropyl acrylamide, N-(2-hydroxyethyl)acrylamide, N-(hydroxymethyl)acrylamide, N-(butoxymethyl)acrylamide, N-[3-(dimethylamino)propyl]acrylamide, N-(1,1-dimethyl-3-oxobutyl)acrylamide, and 2-acrylamide-2-methyl propane sulfonic acid). However, it is difficult to find products that satisfy all of the effects of the present disclosure. The present disclosure is based on a finding that the acrylamide compound represented by general formula (1) satisfies the effects of the present disclosure by having an ester structure having neutrality and an appropriate polarity.

Next, groups of example compounds a to h will be presented below as specific examples of the acrylamide compound represented by general formula (1) above. However, these example compounds are non-limiting examples.

The group of example compounds a includes groups of compounds a1 to a6 presented below. One of these compounds may be used alone or two or more of these compounds may be used in combination.
<<Group of Example Compounds a1>>
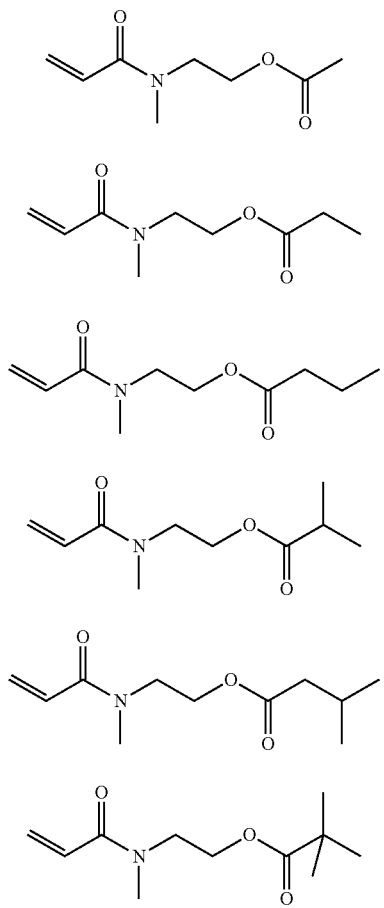
a1-1
a1-2
a1-3
a1-4
a1-5
a1-6
<<Group of Example Compounds a2>>
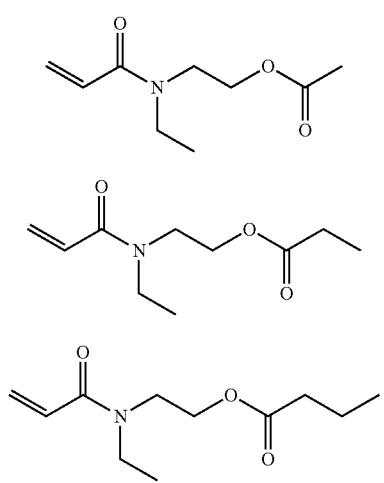
a2-1
a2-2
a2-3
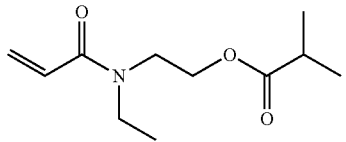
a2-4
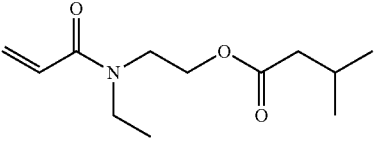
a2-5
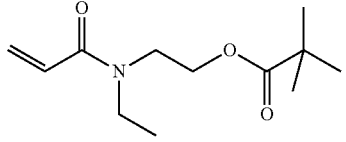
a2-6
<<Group of Example Compounds a3>>
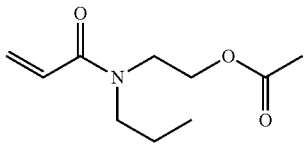
a3-1
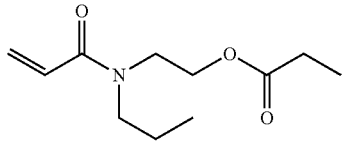
a3-2
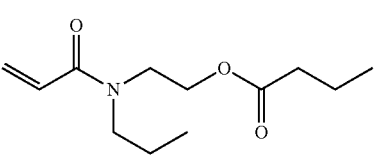
a3-3
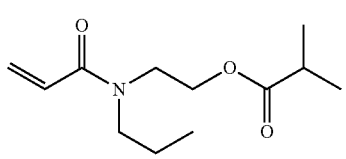
a3-4
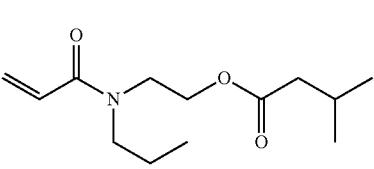
a3-5
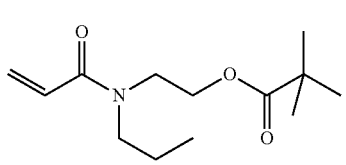
a3-6

<<Group of Example Compounds a4>>
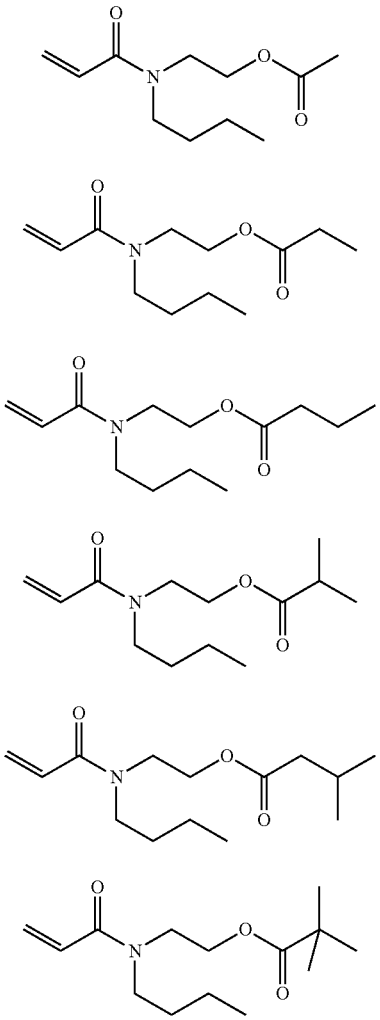
a4-1
a4-2
a4-3
a4-4
a4-5
a4-6
<<Group of Example Compounds a5>>
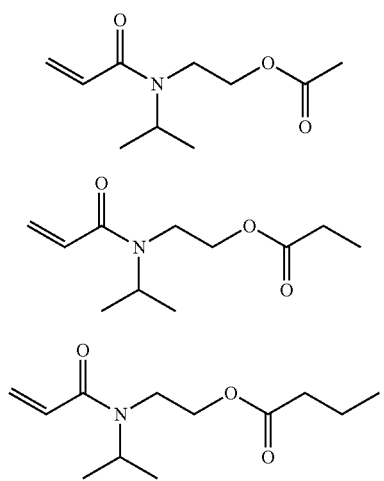
a5-1
a5-2
a5-3
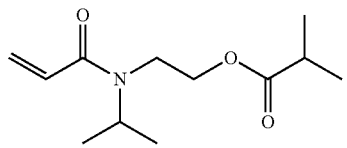
a5-4
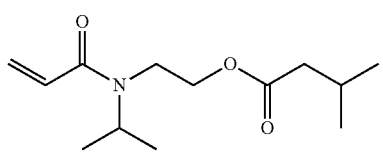
a5-5
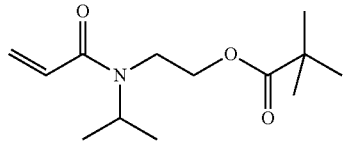
a5-6
<<Group of Example Compounds a6>>
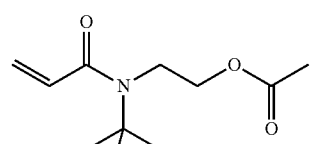
a6-1
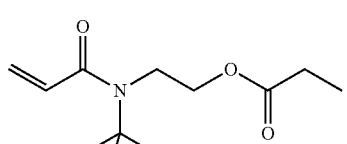
a6-2
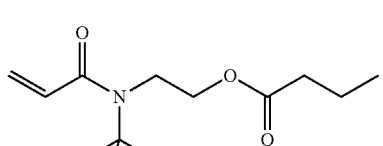
a6-3
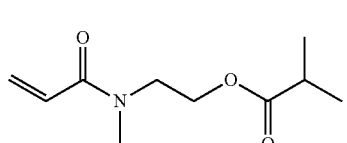
a6-4
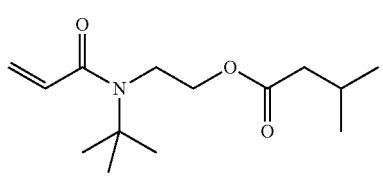
a6-5

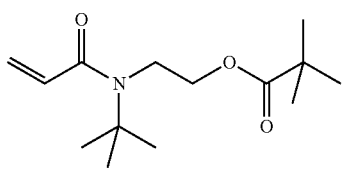
a6-6
The group of example compounds b includes groups of compounds b1 to b6 presented below. One of these compounds may be used alone or two or more of these compounds may be used in combination.
<<Group of Example Compounds b1>>
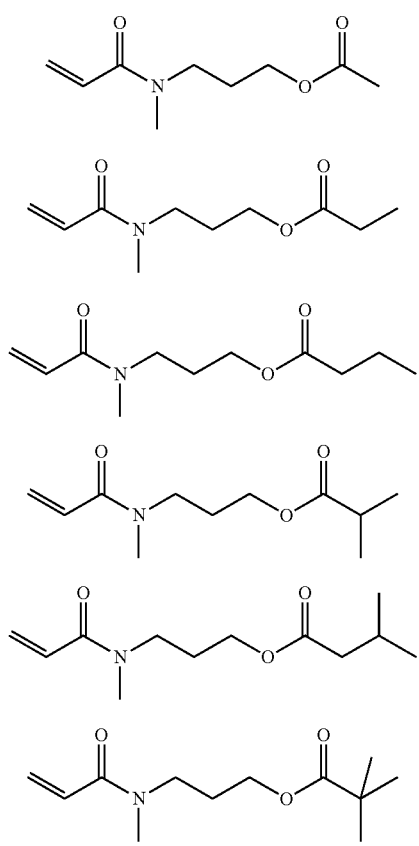
b1-1
b1-2
b1-3
b1-4
b1-5
b1-6
<<Group of Example Compounds b2>>
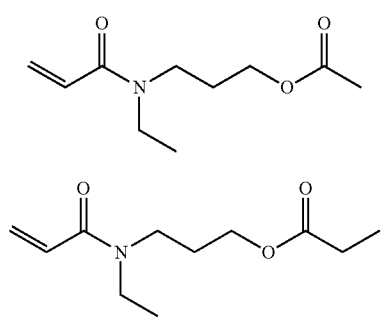
b2-1
b2-2
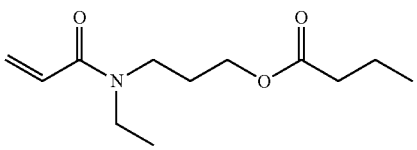
b2-3
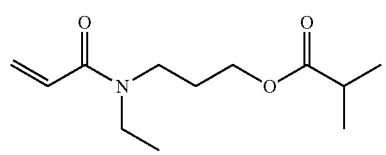
b2-4
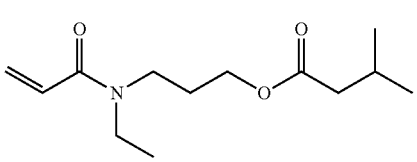
b2-5
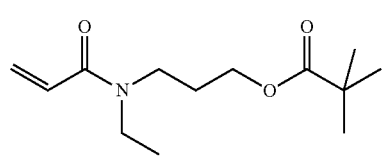
b2-6
<<Group of Example Compounds b3>>
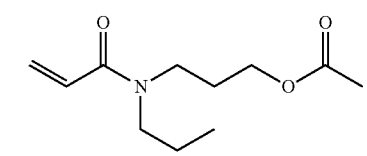
b3-1
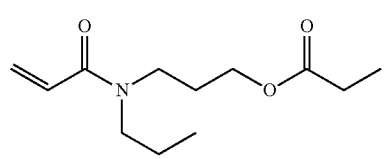
b3-2
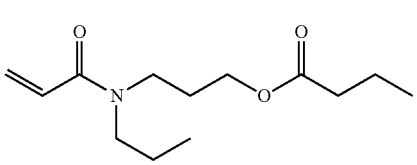
b3-3
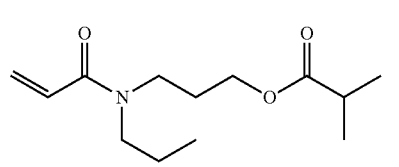
b3-4
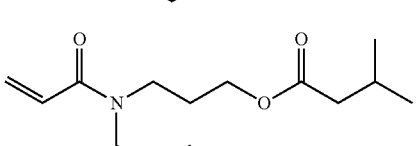
b3-5

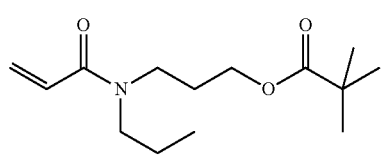
b3-6
<<Group of Example Compounds b4>>
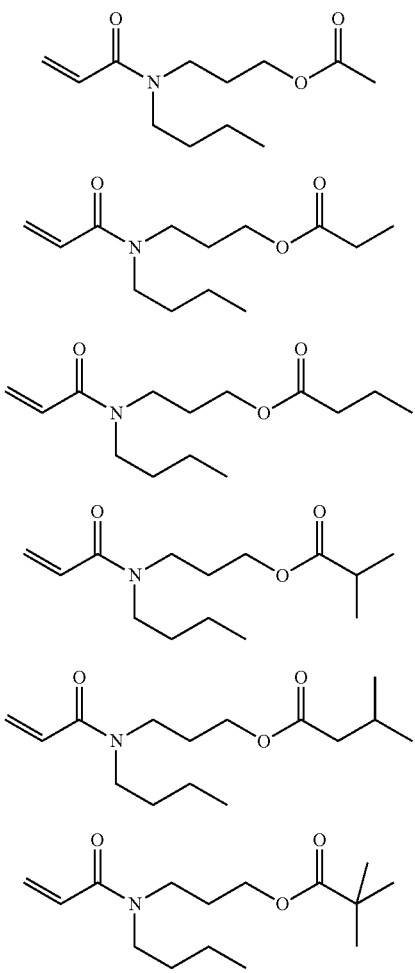
b4-1
b4-2
b4-3
b4-4
b4-5
b4-6
<<Group of Example Compounds b5>>
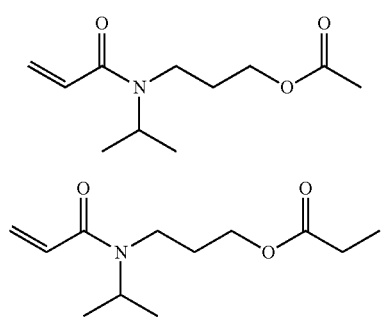
b5-1
b5-2
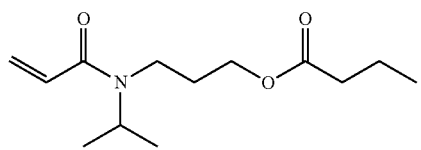
b5-3
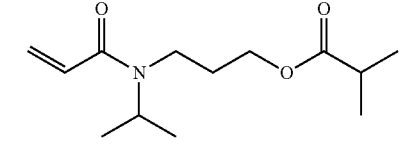
b5-4
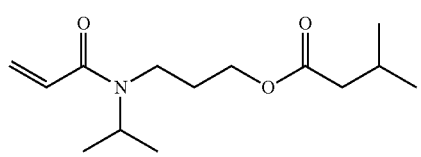
b5-5
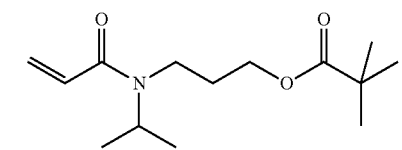
b5-6
<<Group of Example Compounds b6>>
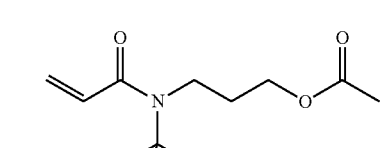
b6-1
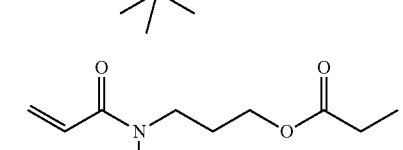
b6-2
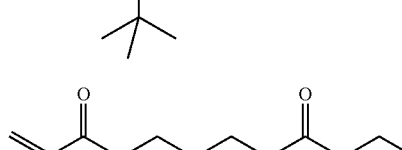
b6-3
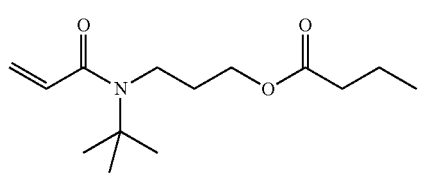
b6-4
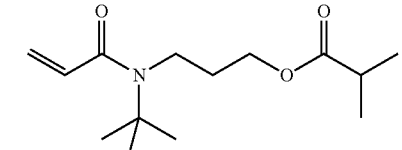
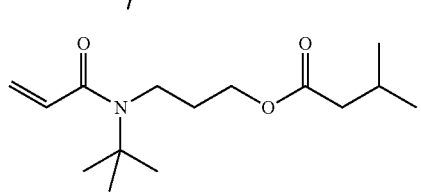
b6-5

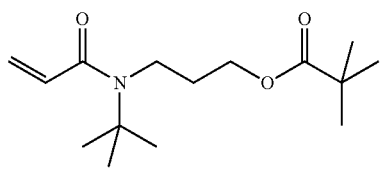
b6-6
The group of example compounds c includes groups of compounds c1 to c6 presented below. One of these compounds may be used alone or two or more of these compounds may be used in combination.
<<Group of Example Compounds c1>>
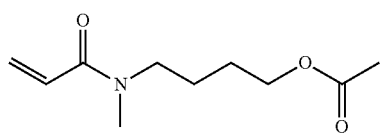
c1-1
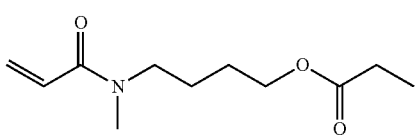
c1-2
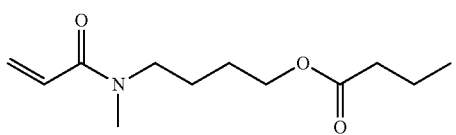
c1-3
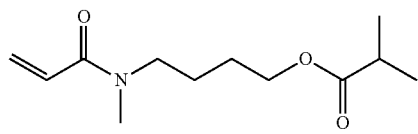
c1-4
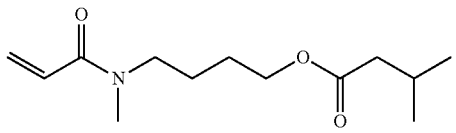
c1-5
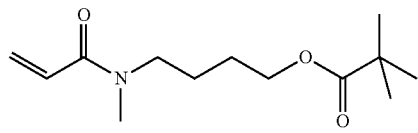
c1-6
<<Group of Example Compounds c2>>
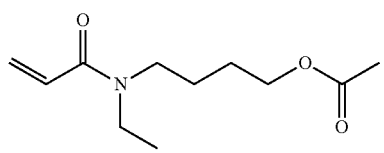
c2-1
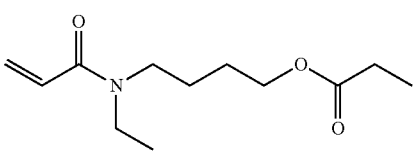
c2-2
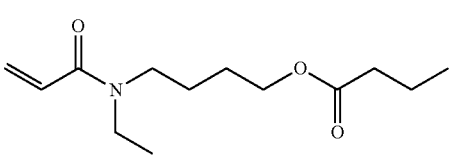
c2-3
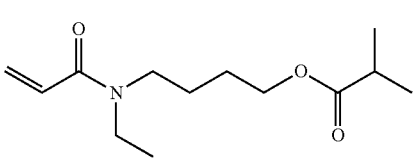
c2-4
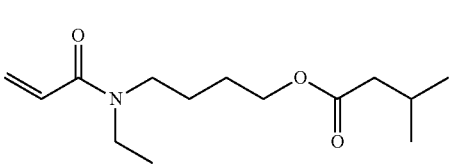
c2-5
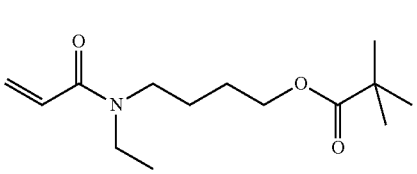
c2-6
<<Group of Example Compounds c3>>
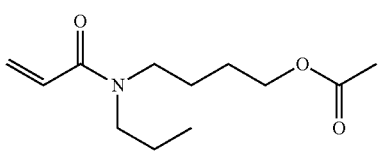
c3-1
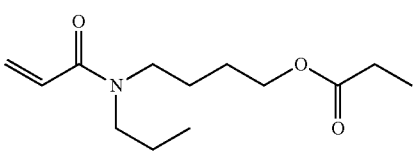
c3-2
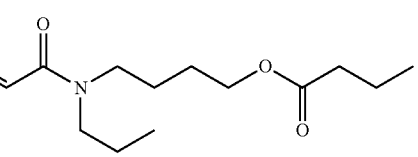
c3-3
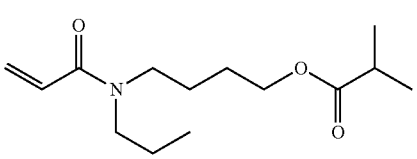
c3-4 c3-5
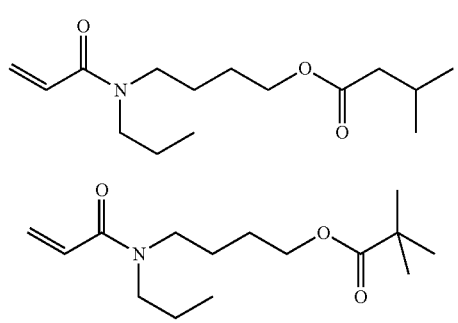
c3-6
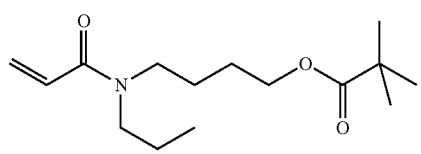
<<Group of Example Compounds c4>>
c4-1
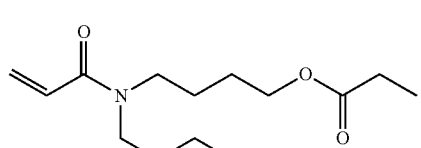
c4-2
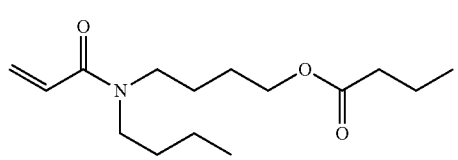
c4-3
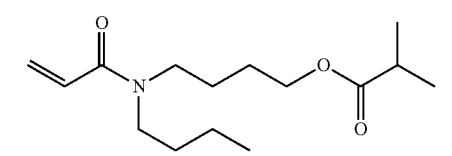
c4-4
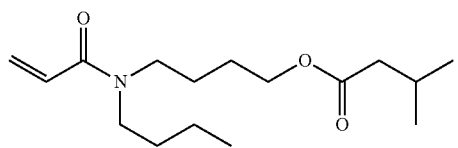
c4-5
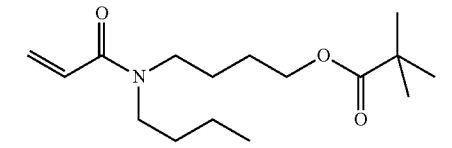
c4-6
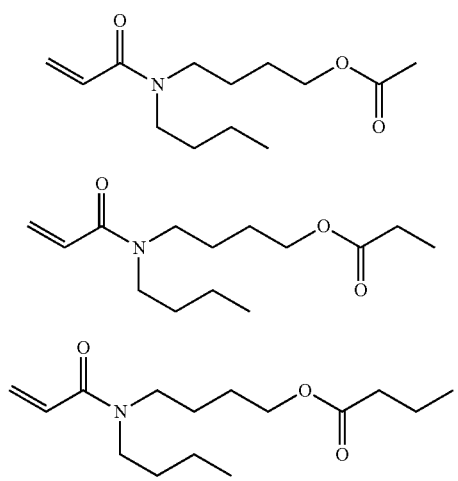
<<Group of Example Compounds c5>>
c5-1
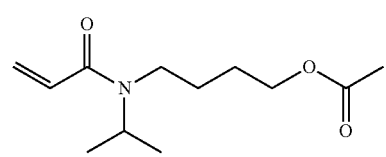
c5-2
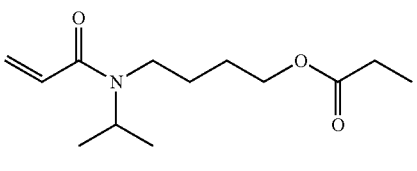
c5-3
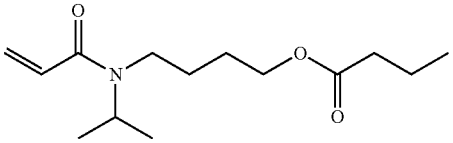
c5-4
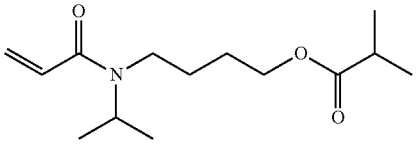
c5-5
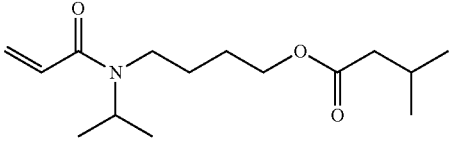
c5-6
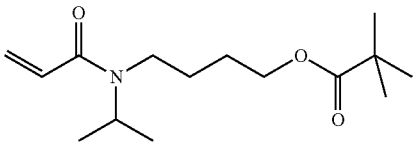
<<Group of Example Compounds c6>>
c6-1
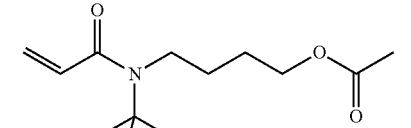
c6-2
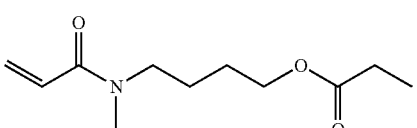
c6-3
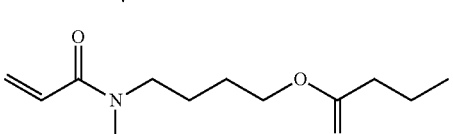
c6-4

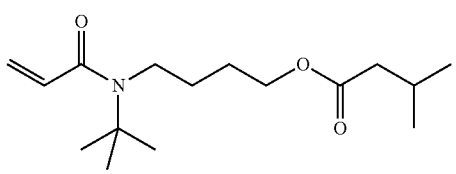
c6-5
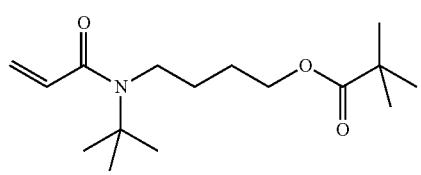
c6-6
The group of example compounds d includes groups of compounds d1 to d6 presented below. One of these compounds may be used alone or two or more of these compounds may be used in combination.
<<Group of Example Compounds d1>>
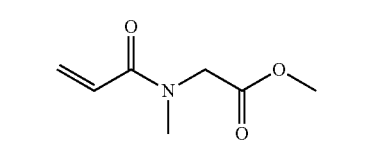
d1-1
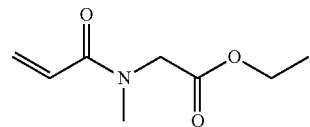
d1-2
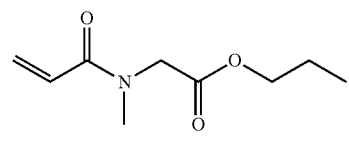
d1-3
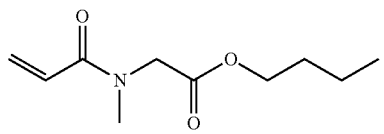
d1-4
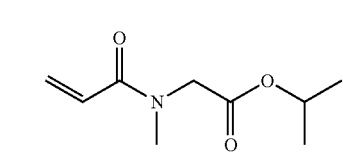
d1-5
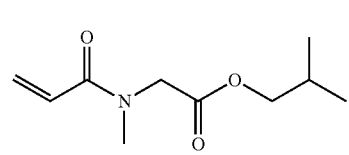
d1-6
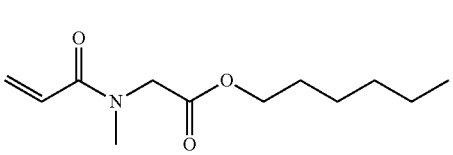
d1-7
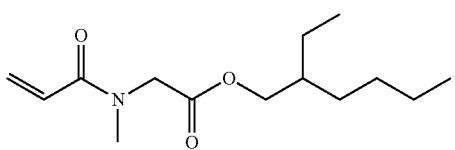
d1-8
<<Group of Example Compounds d2>>
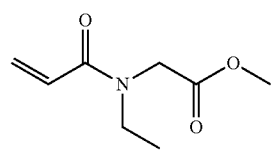
d2-1
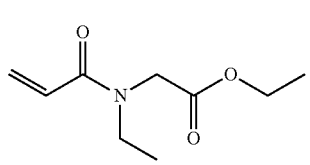
d2-2
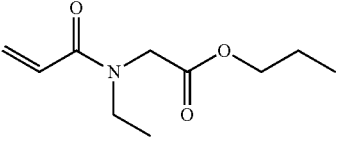
d2-3
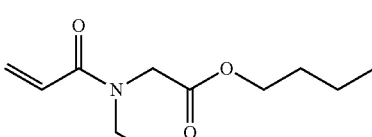
d2-4
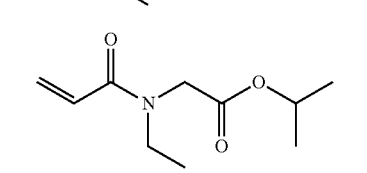
d2-5
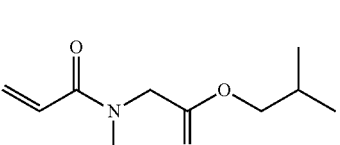
d2-6
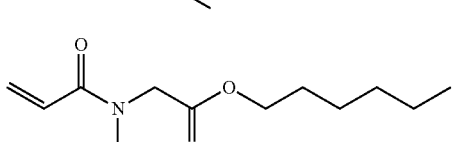
d2-7
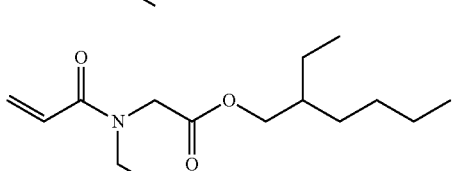
d2-8

<<Group of Example Compounds d3>>
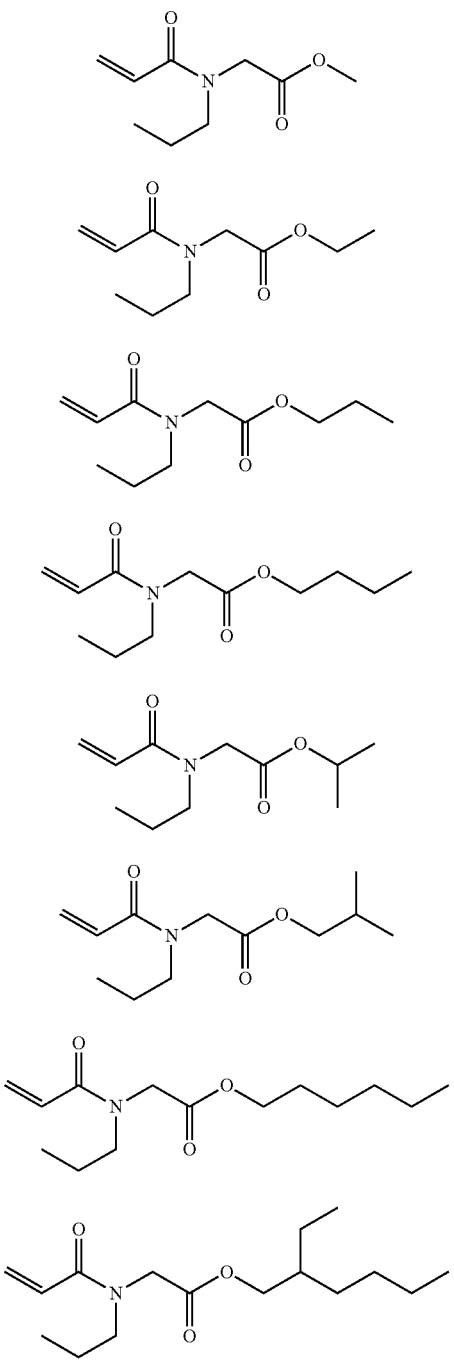
<<Group of Example Compounds d4>>
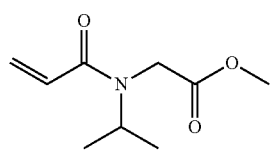
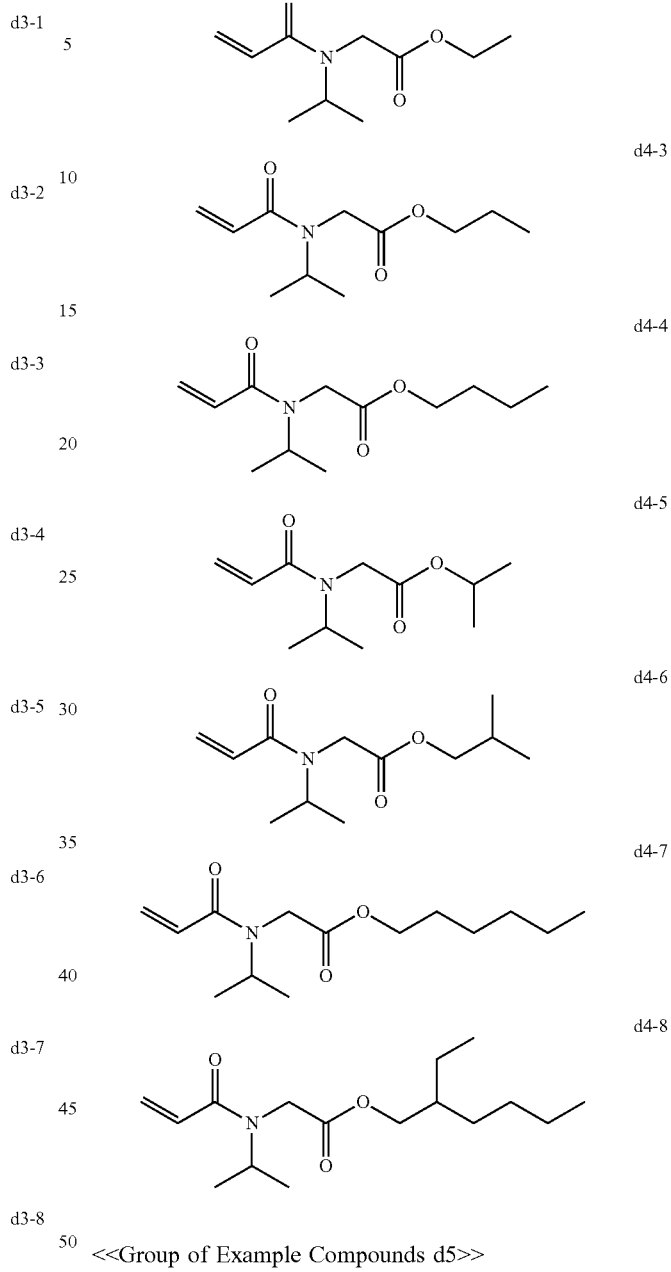
<<Group of Example Compounds d5>>

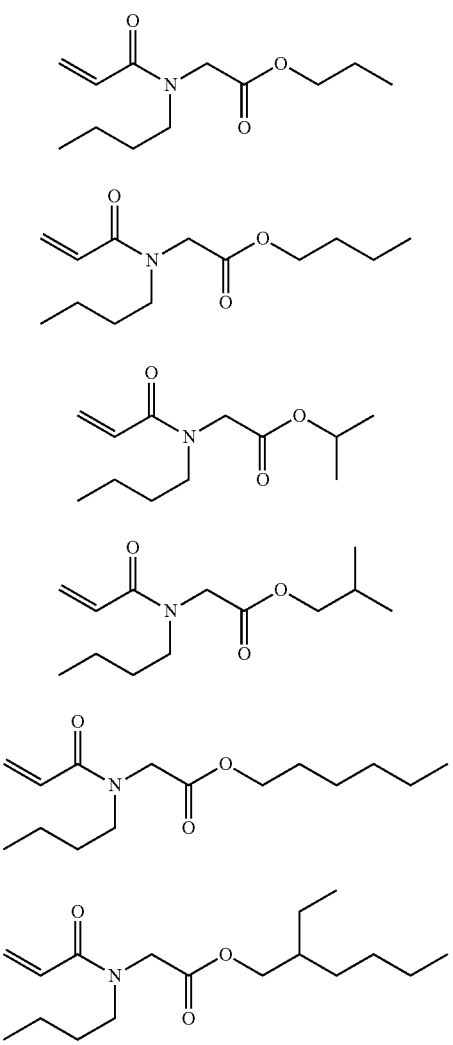
<<Group of Example Compounds d6>>
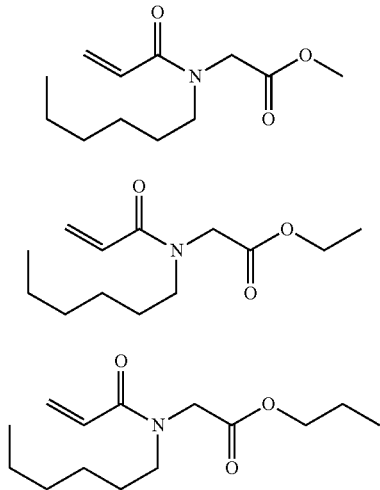
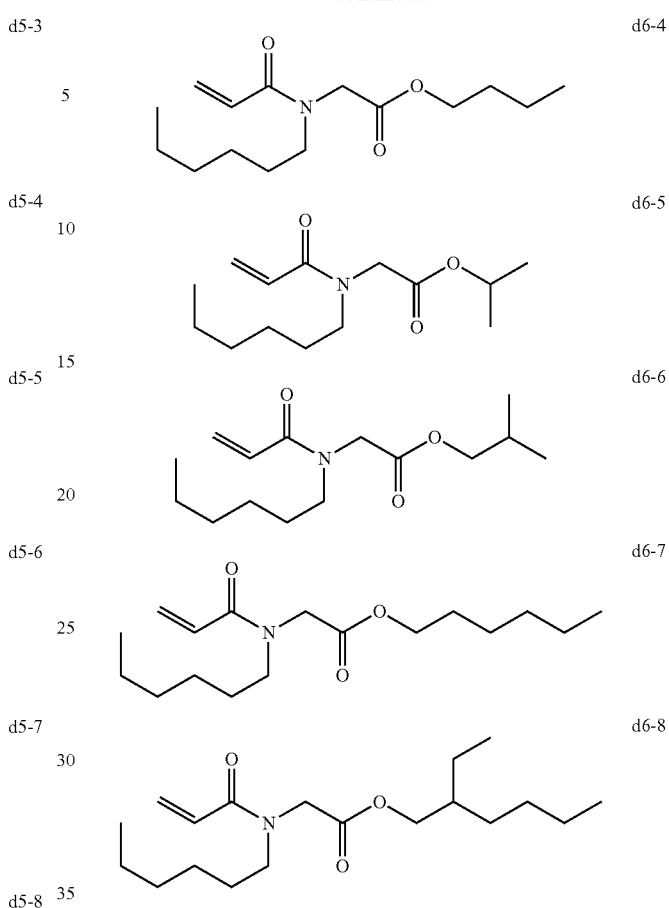
The group of example compounds e includes groups of compounds e1 to e6 presented below. One of these compounds may be used alone or two or more of these compounds may be used in combination.
<<Group of Example Compounds e1>>
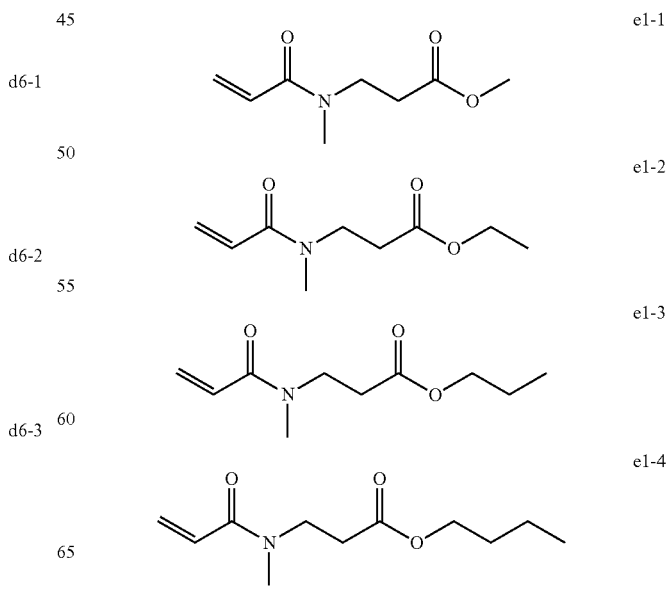

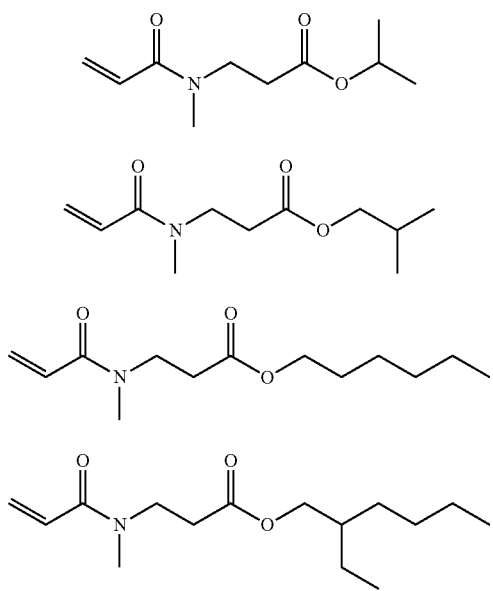
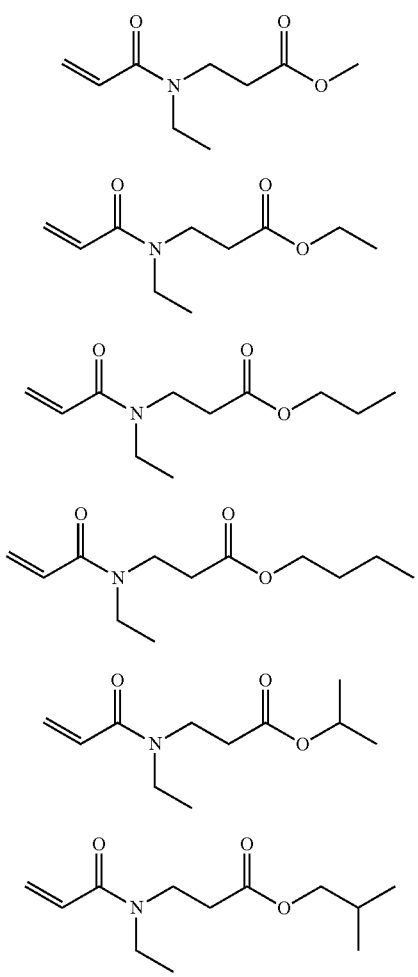
<<Group of Example Compounds e2>>
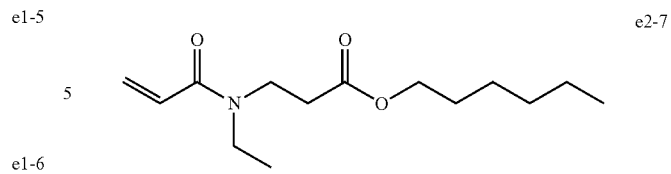
<<Group of Example Compounds e3>>
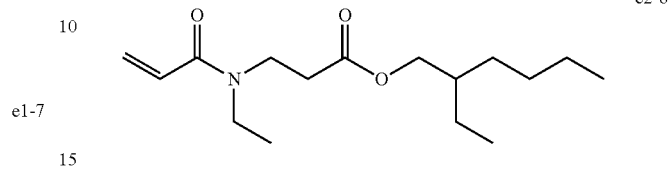
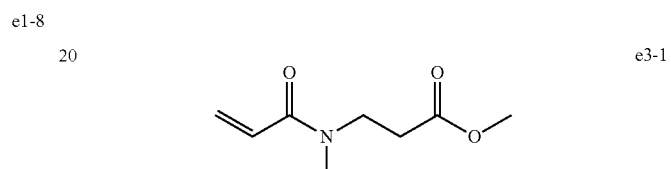
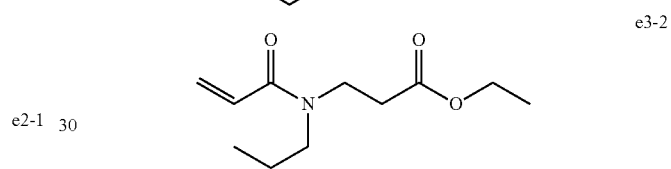
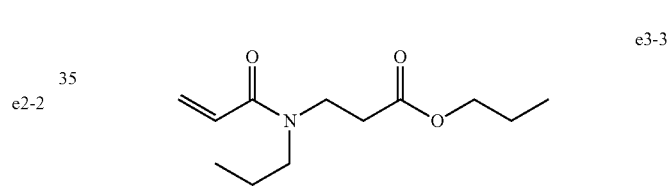
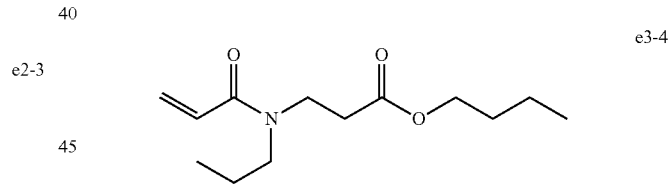

e3-8
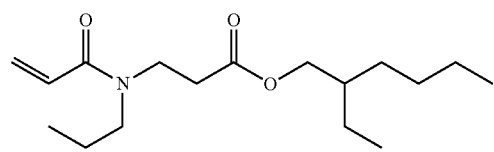
<<Group of Example Compounds e4>>
e4-1
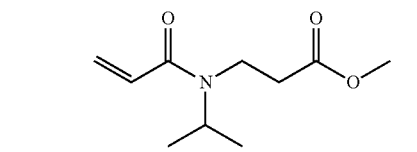
e4-2
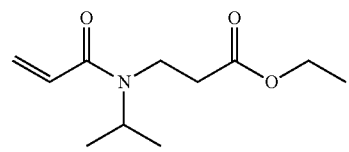
e4-3
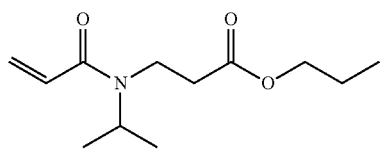
e4-4
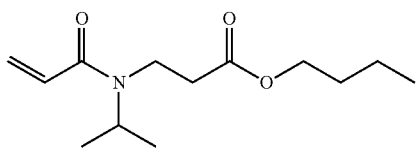
e4-5
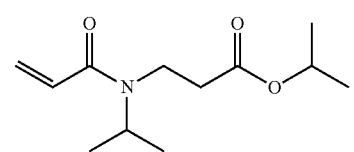
e4-6
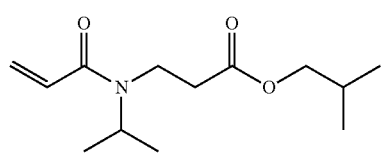
e4-7
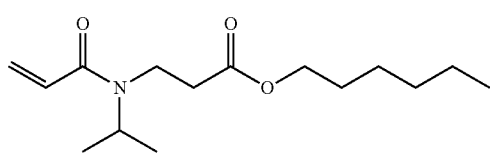
e4-8
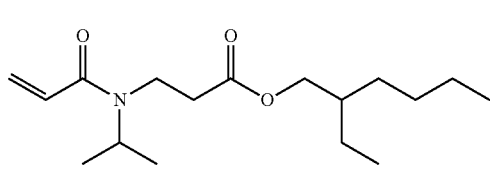
<<Group of Example Compounds e5>>
e5-1
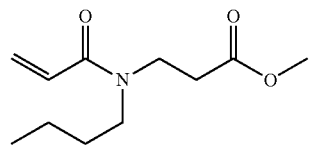
e5-2
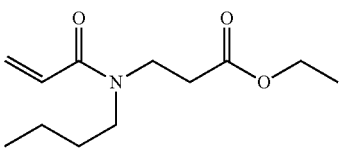
e5-3
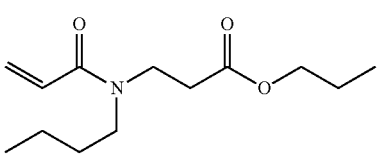
e5-4
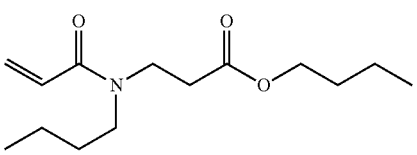
e5-5
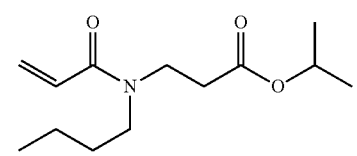
e5-6
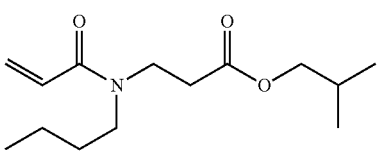
e5-7
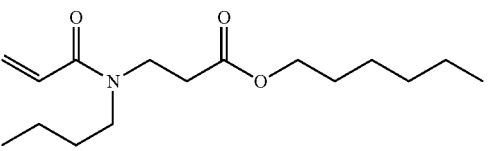
e5-8
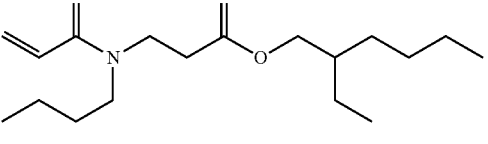
<<Group of Example Compounds e6>>
e6-1
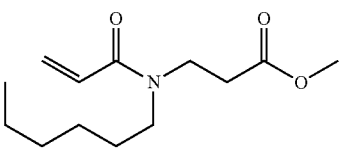

-continued

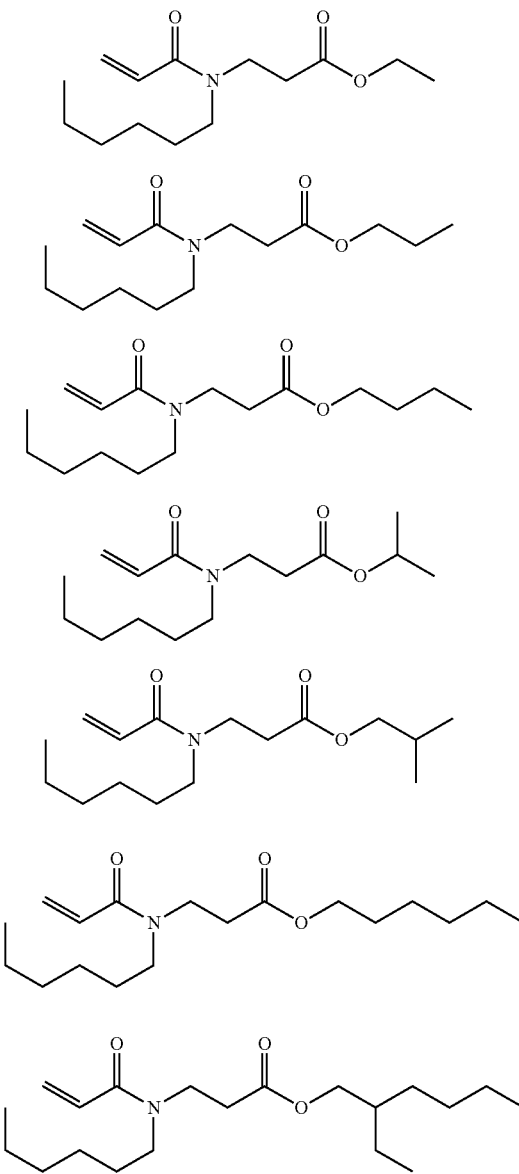

The group of example compounds f includes a group of compounds f1 presented below. One of these compounds may be used alone or two or more of these compounds may be used in combination.

<<Group of Example Compounds f1>>

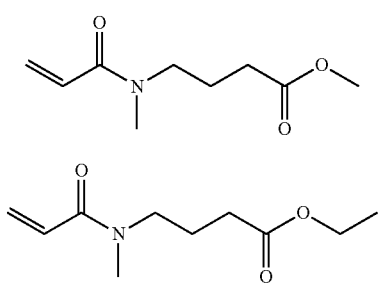

-continued

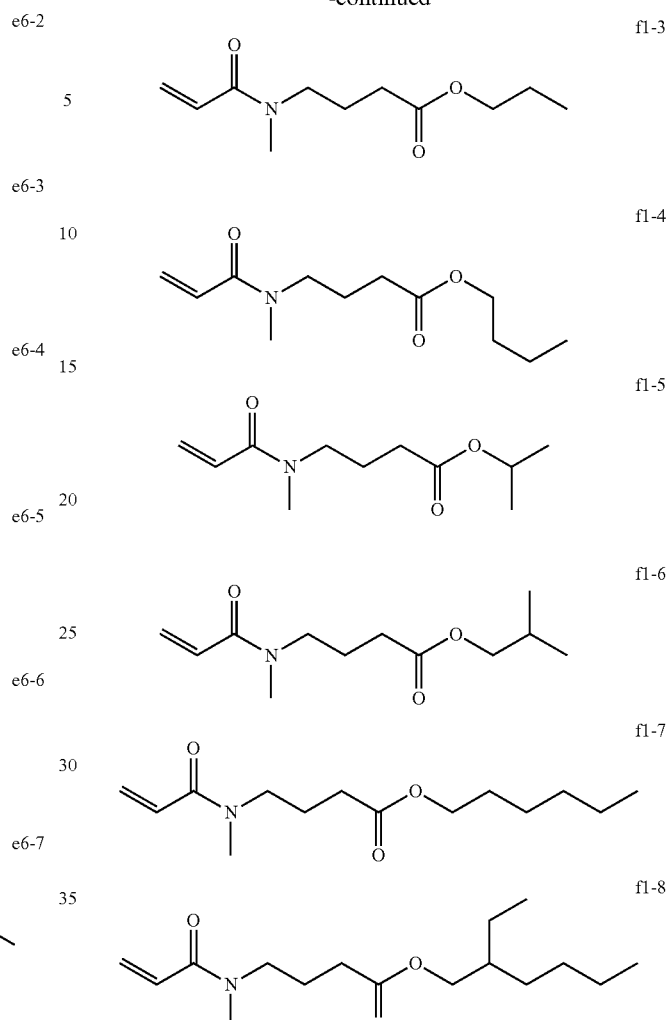

The group of example compounds g includes groups of compounds g1 to g6 presented below. One of these compounds may be used alone or two or more of these compounds may be used in combination.

<<Group of Example Compounds g1>>

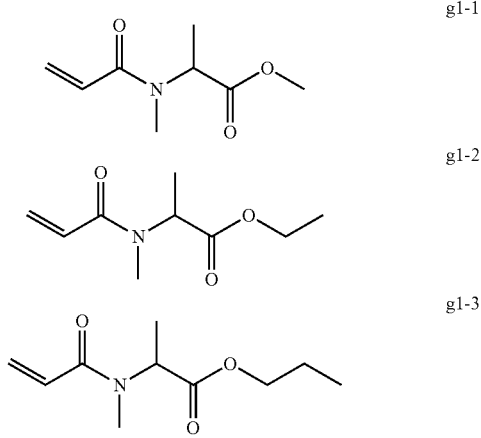

-continued
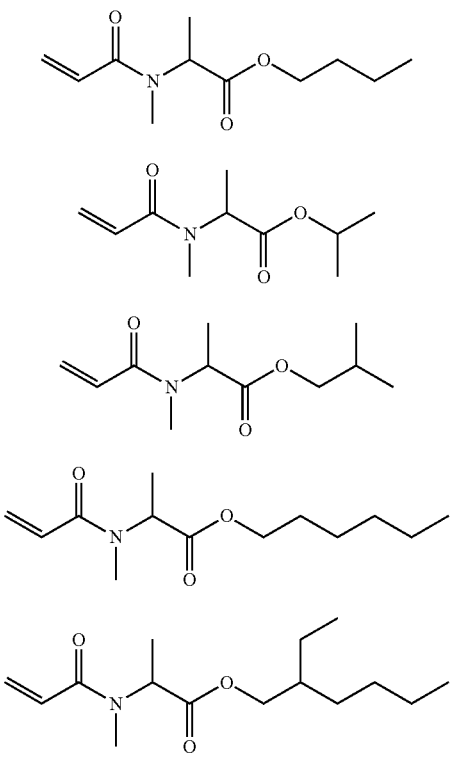
g1-4
g1-5
g1-6
g1-7
g1-8
<<Group of Example Compounds g2>>
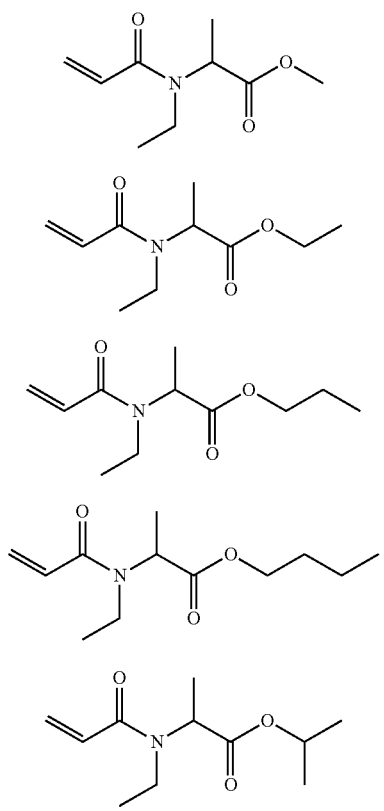
g2-1
g2-2
g2-3
g2-4
g2-5
-continued
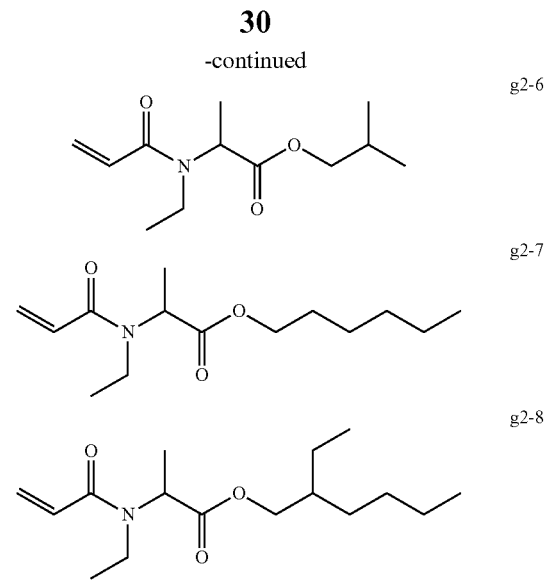
g2-6
g2-7
g2-8
<<Group of Example Compounds g3>>
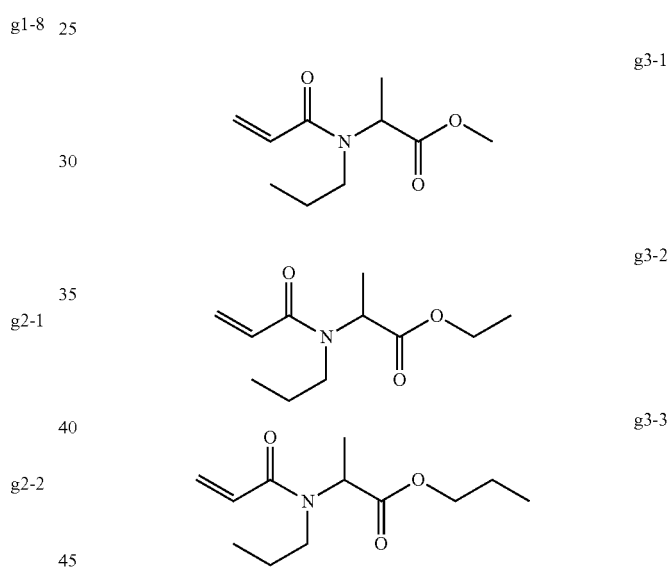
g3-1
g3-2
g3-3
g3-4
g3-5
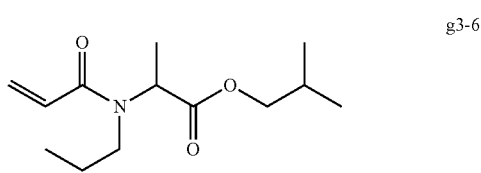
g3-6

<<Group of Example Compounds g4>>
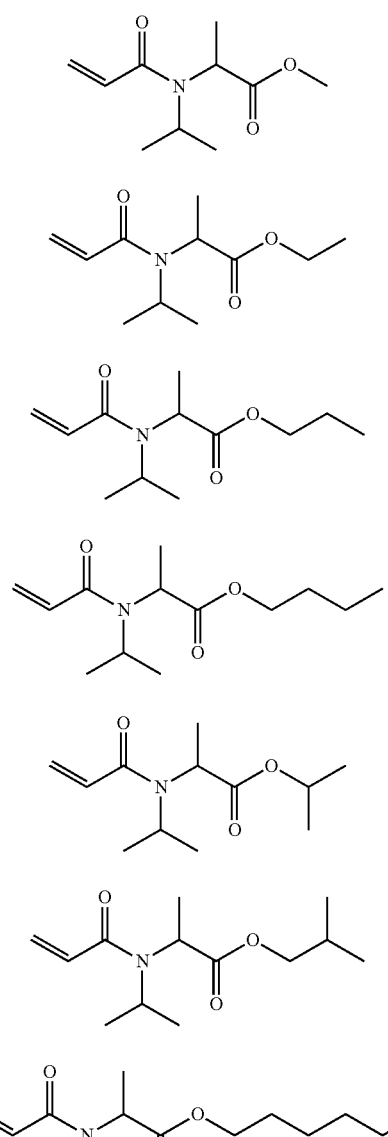
g3-7
g3-8
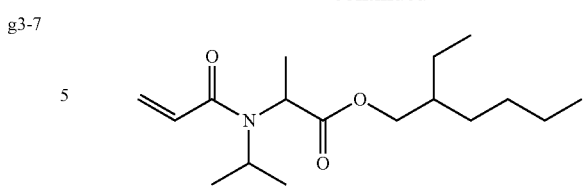 g4-8
<<Group of Example Compounds g5>>
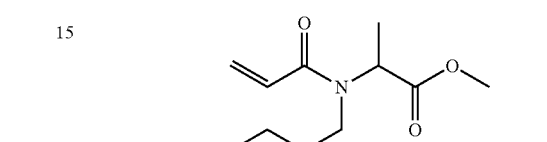 g5-1
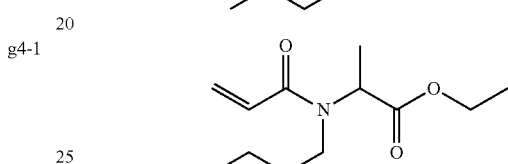 g5-2
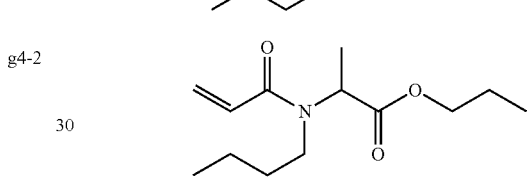 g5-3
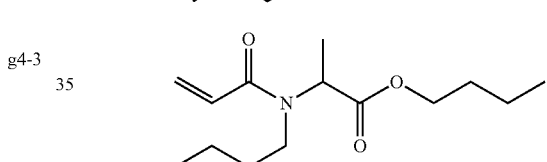 g5-4
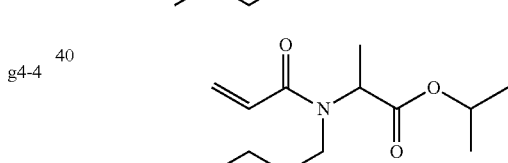 g5-5
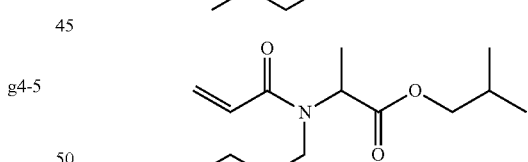 g5-6
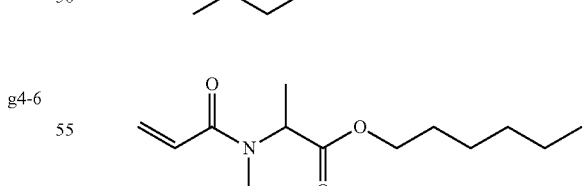 g5-7
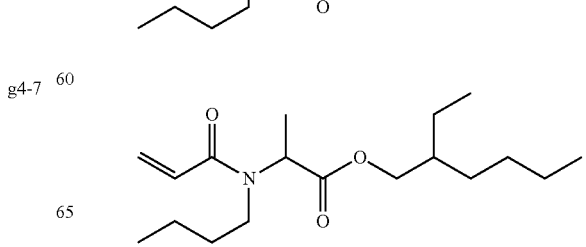 g5-8

<<Group of Example Compounds g6>>

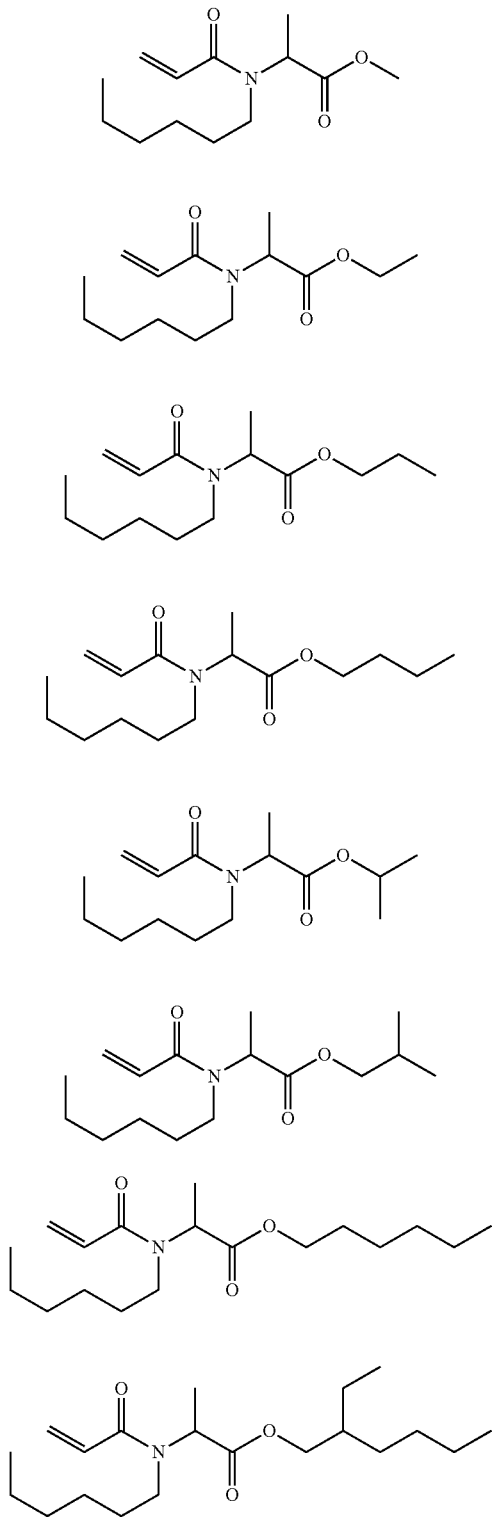

The group of example compounds h includes a group of compounds h1 presented below. One of these compounds may be used alone or two or more of these compounds may be used in combination.

<<Group of Example Compounds H1>>

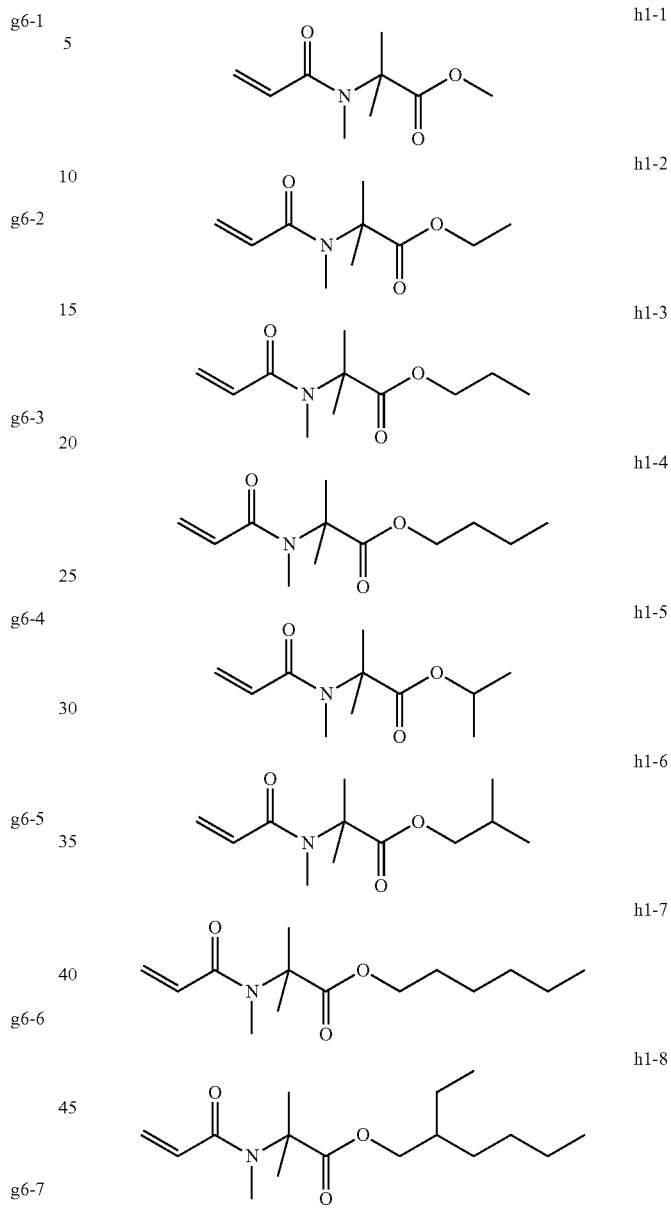

Among the groups of example compounds a to h, the example compound a1-1, the example compound a1-4, the example compound a6-1, the example compound d1-1, the example compound d1-2, the example compound d1-4, the example compound d1-5, the example compound d3-2, the example compound d4-1, the example compound d4-5, the example compound d6-1, the example compound d6-4, the example compound g1-1, the example compound g1-2, and the example compound g1-5 are preferable, and the example compound g1-1, the example compound d1-2, the example compound g1-1, the example compound g1-2, and the example compound g1-5 are more preferable in terms of curability.

As the acrylamide compound represented by general formula (1) above, two or more different compounds may be used as a mixture. In this case, examples of a different compound include a structural isomer. The mixing ratio is not particularly limited.

The content of the acrylamide compound is 20% by mass or greater but 50% by mass or less, preferably 23% by mass or greater but 45% by mass or less, and more preferably 30% by mass or greater but 45% by mass or less relative to the total amount of the composition.

When the content of the acrylamide compound is 20% by mass or greater but 50% by mass or less, there is an advantage that curability is excellent.

<Multifunctional Monomer>

The multifunctional monomer is not particularly limited and may be appropriately selected depending on the intended purpose. Examples of the multifunctional monomer include multifunctional radically polymerizable compounds, multifunctional cationically polymerizable compounds, and multifunctional anionically polymerizable compounds. One of these multifunctional monomers may be used alone or two or more of these multifunctional monomers may be used in combination.

The multifunctional monomer is not particularly limited and may be appropriately selected depending on the intended purpose, so long as the multifunctional monomer is a multifunctional monomer that is bifunctional or greater but hexafunctional or less. Examples of the multifunctional monomer include neopentyl glycol diacrylate, ethoxylated neopentyl glycol diacrylate propoxylated neopentyl glycol diacrylate, 1,6-hexanediol diacrylate, ethylene glycol diacrylate, diethylene glycol diacrylate, triethylene glycol diacrylate, tetraethylene glycol diacrylate, polyethylene glycol diacrylate, propylene glycol diacrylate, dipropylene glycol diacrylate, tripropylene glycol diacrylate, tetrapropylene glycol diacrylate, polypropylene glycol diacrylate, pentaerythritol triacrylate, is pentaerythritol tetra(meth)acrylate, dipentaerythritol tetra(meth)acrylate, trimethylolpropane triacrylate, tetramethylolmethane tetraacrylate, 1,6-hexanediol dimethacrylate, ethylene glycol dimethacrylate, triethylene glycol dimethacrylate, polyethylene glycol dimethacrylate, polypropylene glycol dimethacrylate, trimethylolethane trimethacrylate, trimethylolpropane trimethacrylate, ethylene glycol divinyl ether, diethylene glycol divinyl ether, triethylene glycol divinyl ether, propylene glycol divinyl ether, dipropylene glycol divinyl ether, butanediol divinyl ether, hexanediol divinyl ether, cyclohexane dimethanol divinyl ether, neopentyl glycol hydroxypivalate diacrylate, tetramethylolmethane triacrylate, dimethylol tricyclodecane di(meth)acrylate, modified glycerin tri(meth)acrylate, modified bisphenol A di(meth)acrylate, bisphenol A-propylene oxide adduct di(meth)acrylate, bisphenol A-ethylene oxide adduct di(meth)acrylate, dipentaerythritol hexa(meth)acrylate, ditrimethylolpropane tetra(meth)acrylate, caprolactone-modified pentaerythritol hexa(meth)acrylate, and glycerin (meth)acrylate. One of these multifunctional monomers may be used alone or two or more of these multifunctional monomers may be used in combination.

Among these multifunctional monomers, caprolactone-modified pentaerythritol hexa(meth)acrylate is preferable.

The content of the multifunctional monomer is 40% by mass or greater but 70% by mass or less, preferably 45% by mass or greater but 67% by mass or less, and more preferably 50% by mass or greater but 65% by mass or less relative to the total amount of the composition.

When the content of the multifunctional monomer is 40% by mass or greater but 70% by mass or less, there is an advantage that durability is excellent.

<Other Polymerizable Compounds than Acrylamide Compound Represented by General Formula (1) and Multifunctional Monomer>

Other polymerizable compounds than the acrylamide compound represented by general formula (1) and the multifunctional monomer are not particularly limited and may be appropriately selected depending on the intended purpose. Examples of the other polymerizable compounds include radically polymerizable compounds, cationically polymerizable compounds, and anionically polymerizable compounds. One of these polymerizable compounds may be used alone or two or more of these polymerizable compounds may be used in combination.

The radically polymerizable compounds are not particularly limited and may be appropriately selected depending on the intended purpose, so long as the radically polymerizable compounds are compounds containing one or more radically polymerizable ethylenic unsaturated groups. Examples of the radically polymerizable compounds include compounds encompassing monomers, oligomers, and polymers. Among these radically polymerizable compounds, unsaturated carboxylic acids such as acrylic acid, methacrylic acid, itaconic acid, crotonic acid, isocrotonic acid, and maleic acid, salts of these unsaturated carboxylic acids, or compounds derived from these unsaturated carboxylic acids and the salts of these unsaturated carboxylic acids, anhydrides containing an ethylenic unsaturated group, acrylonitrile, styrene, unsaturated polyester, unsaturated polyether, unsaturated polyamide, and unsaturated urethane are preferable.

Examples of the radically polymerizable compounds include: acrylic acid derivatives such as 2-hydroxyethyl acrylate, butoxyethyl acrylate, carbitol acrylate, cyclohexyl acrylate, tetrahydrofurfuryl acrylate, benzyl acrylate, bis(4-acryloxypolyethoxyphenyl)propane, and epoxy acrylate; methacrylic acid derivatives such as methyl methacrylate, n-butyl methacrylate, allyl methacrylate, glycidyl methacrylate, benzyl methacrylate, dimethyl aminomethyl methacrylate, and 2,2-bis(4-methacryloxypolyethoxyphenyl)propane; acrylamide derivatives such as N-methylolacrylamide, diacetone acrylamide, 2-hydroxyethyl acrylamide, and acryloylmorpholine; allyl compound derivatives such as allyl glycidyl ether, diallyl phthalate, and triallyl trimellitate; monovinyl ether compounds, divinyl ether compounds, or trivinyl ether compounds such as ethylene glycol monovinyl ether, triethylene glycol monovinyl ether, hydroxyethyl monovinyl ether, hydroxynonyl monovinyl ether, and trimethylolpropane trivinyl ether; monovinyl ether compounds such as ethyl vinyl ether, n-butyl vinyl ether, isobutyl vinyl ether, octadecyl vinyl ether, cyclohexyl vinyl ether, hydroxybutyl vinyl ether, 2-ethylhexyl vinyl ether, cyclohexane dimethanol monovinyl ether, n-propyl vinyl ether, isopropyl vinyl ether, isopropenyl ether-o-propylene carbonate, dodecyl vinyl ether, diethylene glycol monovinyl ether, and octadecyl vinyl ether; 2-ethylhexyl diglycol acrylate; 2-hydroxy-3-phenoxypropyl acrylate; 2-hydroxybutyl acrylate; 2-acryloyloxy ethyl phthalic acid; methoxypolyethylene glycol acrylate; 2-acryloyloxyethyl-2-hydroxyethyl phthalic acid; ethoxylated phenyl acrylate; 2-acryloyloxyethyl succinic acid; nonyl phenol-ethylene oxide adduct acrylate; bisphenol A diglycidyl ether acrylic acid adduct; phenoxypolyethylene glycol acrylate; 2-acryloyloxyethyl hexahydrophthalic acid; tolylene diisocyanato urethane polymers; lactone-modified flexible acrylate; butoxyethyl acrylate; propylene glycol diglycidyl ether acrylic acid adduct; hexamethylene diisocyanato urethane polymers; methoxydipropylene glycol acrylate; stearyl acrylate; isoamyl acrylate; isomyristyl acrylate; isostearyl acrylate; lactone-modified acrylate; and (meth)acryloylmorpholine. One of these radically polymerizable compounds may be used alone or two or more of these radically polymerizable compounds may be used in combination.

Examples of the cationically polymerizable compounds include epoxy compounds, vinyl ether compounds, and oxetane compounds. One is of these cationically polymerizable compounds may be used alone or two or more of these cationically polymerizable compounds may be used in combination.

Examples of the anionically polymerizable compounds include epoxy compounds, lactone compounds, acrylic compounds, and methacrylic compounds. One of these anionically polymerizable compounds may be used alone or two or more of these anionically polymerizable compounds may be used in combination. Among these polymerizable compounds, the acrylic acid derivatives and the methacrylic acid derivatives raised as examples of the radically polymerizable compounds are preferable.

The content of the other polymerizable compounds is preferably 0.01 parts by mass or greater but 100 parts by mass or less and more preferably 0.1 parts by mass or greater but 50 parts by mass or less relative to 100 parts by mass of the acrylamide compound represented by general formula (1) above.

<Polymerization Initiator>

The polymerization initiator may be any substance that can produce active species such as radicals and cations in response to energy and initiate polymerization of a polymerizable compound (e.g., a monomer and an oligomer). As such a polymerization initiator, one, or two or more in combination, selected from, for example, known radical polymerization initiators, cationic polymerization initiators, and base generators may be used. Above all, it is preferable to use radical polymerization initiators.

Examples of radical polymerization initiators include aromatic ketones, acylphosphine oxide compounds, aromatic onium salt compounds, organic peroxides, thio compounds (e.g., thioxanthone compounds and thiophenyl group-containing compounds), hexaaryl biimidazole compounds, ketoxime ester compounds, borate compounds, adinium compounds, metallocene compounds, active ester compounds, carbon-halogen bond-containing compounds, and alkylamine compounds.

Specific examples of radical polymerization initiators include bis(2,4,6-trimethylbenzoyl)-phenylphosphine oxide (available from BASF Japan Ltd., product name: IRGACURE 819), 2-methyl-1-(4-methylthiophenyl)-2-morpholinopropan-1-one (available from BASF Japan Ltd., product name: IRGACURE 907), 1-hydroxy-cyclohexyl-phenyl-ketone (available from BASF Japan Ltd., product name: IRGACURE 184), and bis(2,4,6-trimethylbenzoyl)-phenylphosphine oxide (available from BASF Japan Ltd., product name: IRGACURE 819).

The content of the polymerization initiator is preferably 1% by mass or greater but 20% by mass or less, preferably 3% by mass or greater but 15% by mass or less, and more preferably 5% by mass or greater but 10% by mass or less relative to the total amount of the composition in terms of achieving a sufficient curing speed.

A polymerization promoter may be used in combination with the polymerization initiator. The polymerization promotor is not particularly limited and may be appropriately selected depending on the intended purpose. Examples of the polymerization promotor include trimethylamine, methyl dimethanolamine, triethanolamine, p-diethylamino-acetophenone, ethyl p-dimethyl aminobenzoate, p-dimethylamino benzoic acid-2-ethyl hexyl, N,N-dimethyl benzyl amine, and 4,4'-bis(diethylamino)benzophenone.

The content of the polymerization promotor is not particularly limited and may be appropriately set depending on the polymerization initiator used and the amount of the polymerization initiator.

Examples of the cationic polymerization initiator include $B(C_6F_5)_4$-, $PF_6$-, $AsF_6$-, $SbF_6$-, and $CF_3SO_3$-salts of, for example, diazonium, ammonium, iodonium, sulfonium, and phosphonium, sulfonates that can produce sulfonic acid, halides that can produce hydrogen halide, and iron allene complexes.

Examples of the anionic polymerization initiator include o-nitrobenzyl carbamate derivatives, o-acyloxyl derivatives, and o-carbamoyl oxime amidine derivatives.

Examples of combination of the other polymerizable compound and the polymerization initiator include combination of the radically polymerizable compound and the radical polymerization initiator, combination of the cationically polymerizable compound and the cationic polymerization inititator, and combination of the anionically polymerizable compound and the anionic polymerization initiator.

The composition of the present disclosure may further contain a sensitizer in order to promote decomposition of a photopolymerization initiator by active energy ray irradiation.

The sensitizer absorbs active energy rays to become an electroexcited state and contacts the polymerization initiator while in that state, to promote a chemical change (decomposition, or production of radicals, acids, or bases) of the polymerization initiator by the action of, for example, electron transfer, energy transfer, and heat generation. The mass ratio of the sensitizer relative to the photopolymerization initiator is preferably $5 \times 10^{-3}$ or greater but 200 or less, and more preferably 0.02 or greater but 50 or less.

The sensitizer is not particularly limited and may be appropriately selected depending on the intended purpose. It is preferable to use a sensitizing pigment having an absorption wavelength in a wavelength range of 350 nm or greater but 450 nm or less.

Examples of the sensitizer include polynuclear aromatic series (e.g., pyrene, perylene, and triphenylene), xanthenes (e.g., fluorescein, eosin, erythrosine, rhodamine B, and rose Bengal), cyanines (e.g., thiacarbocyanine and oxacarbocyanine), merocyanines (e.g., merocyanine and carbomerocyanine), thiazines (e.g., thionine, methylene blue, and toluidine blue), acridines (e.g., acridine orange, chloro flavin, and acriflavine), anthraquinones (e.g., anthraquinone), squaryliums (e.g., squarylium), and coumarins (e.g., 7-diethyl amino-4-methyl coumarin).

The composition of the present disclosure may further contain a co-sensitizer. The co-sensitizer further improves sensitivity of a sensitizing pigment to active energy rays or suppresses inhibition of polymerization of the polymerizable compound by oxygen.

The co-sensitizer is not particularly limited and may be appropriately selected depending on the intended purpose. Examples of the co-sensitizer include: amine-based compounds such as triethanolamine, p-dimethyl aminobenzoic acid ethyl ester, p-formyl dimethyl aniline, and p-methyl thiodimethyl aniline; thiols such as 2-mercapto benzothiazole, 2-mercapto benzoxazole, 2-mercapto benzoimidazole, 2-mercapto-4(3H)-quinazoline, and β-mercapto naphthalene; and sulfides.

The composition of the present disclosure may further contain a polymerization inhibitor. This can increase the storage property (storage stability) of the composition. This also makes it possible to prevent clogging of a head due to thermal polymerization, in the case of discharging the composition by heating the composition and decreasing is the viscosity of the composition.

The polymerization inhibitor is not particularly limited and may be appropriately selected depending on the intended purpose. Examples of the polymerization inhibitor include hydroquinone, benzoquinone, p-methoxyphenol, TEMPO, TEMPOL, and aluminum-cupferron complex. The content of the polymerization inhibitor is preferably 200 ppm or greater but 20,000 ppm or less relative to the total amount of the composition.

<Other Components>

Examples of other components that may be contained in the composition of the present disclosure as needed include a colorant, an organic solvent, a stabilizer, a plasticizer, a thickener, an antiseptic, a heat dissipating agent, a biocompatible substance, and a fiber reinforcing material.

As the colorant, various pigments and dyes may be used that impart black, white, magenta, cyan, yellow, green, orange, and gloss colors such as gold and silver, depending on the intended purpose of the composition of the present disclosure and requisite properties thereof.

A content of the colorant in the composition is not particularly limited, and may be appropriately determined considering, for example, a desired color density and dispersibility of the colorant in the composition. However, it is preferably from 0.1% by mass to 20% by mass relative to the is total mass of the composition. Incidentally, the composition of the present disclosure does not necessarily contain a colorant but can be clear and colorless. In such a case, for example, such a clear and colorless composition is good for an overcoating layer to protect an image.

The pigment can be either inorganic or organic, and two or more of the pigments can be used in combination.

Specific examples of the inorganic pigments include, but are not limited to, carbon blacks (C.I. Pigment Black 7) such as furnace black, lamp black, acetylene black, and channel black, iron oxides, and titanium oxides.

Specific examples of the organic pigments include, but are not limited to, azo pigments such as insoluble azo pigments, condensed azo pigments, azo lakes, and chelate azo pigments, polycyclic pigments such as phthalocyanine pigments, perylene pigments, perinone pigments, anthraquinone pigments, quinacridone pigments, dioxane pigments, thioindigo pigments, isoindolinone pigments, and quinofuranone pigments, dye chelates (e.g., basic dye chelates, acid dye chelates), dye lakes (e.g., basic dye lakes, acid dye lakes), nitro pigments, nitroso pigments, aniline black, and daylight fluorescent pigments.

In addition, a dispersant is optionally added to enhance the dispersibility of pigment. The dispersant has no particular limit and can be, for example, polymer dispersants conventionally used to prepare pigment dispersion (material).

The dyes include, for example, acidic dyes, direct dyes, reactive dyes, basic dyes, and combinations thereof.

<Organic Solvent>

The composition of the present disclosure optionally contains an organic solvent although it is preferable to spare it. The composition free of an organic solvent, in particular volatile organic compound (VOC), is preferable because it enhances safety at where the composition is handled and makes it possible to prevent pollution of the environment. Incidentally, the organic solvent represents a conventional non-reactive organic solvent, for example, ether, ketone, xylene, ethyl acetate, cyclohexanone, and toluene, which is clearly distinguished from reactive monomers. Furthermore, "free of" an organic solvent means that no organic solvent is substantially contained. The content thereof is preferably less than 0.1 percent by mass.

The plasticizer can impart flexibility to a polymer formed of a monomer. Examples of the plasticizer include polyethylene glycol ester, terminally capped polyester, butyl stearate, lauric acid, dioctyl glutarate, triglyceride, dioctyl oxalate, triethyl phosphate, and acetyl tributyl citrate.

Examples of the thickener include polycyano acrylate, polylactic acid, polyglycolic acid, polycaprolactone, polyacrylic acid alkyl ester, and polymethacrylic acid alkyl ester.

Examples of the antiseptic include hitherto used substances that do not cause a monomer to initiate polymerization, such as potassium sorbate, sodium benzoate, sorbic acid, and chlorocresol.

The fiber reinforcing material is not particularly limited. Examples of the fiber reinforcing material include natural rubbers such as styrene and acrylonitrile or synthetic rubbers for reinforcing shock resistance of the composition.

The stabilizer performs the function of suppressing polymerization of a monomer during storage. Examples of the stabilizer include anionic stabilizer and free radical stabilizers. Examples of the former include metaphosphoric acid, maleic acid, maleic anhydride, alkyl sulfonic acid, phosphorus pentoxide, iron (III) chloride, antimony oxide, 2,4,6-trinitrophenol, thiol, alkyl sulfonyl, alkyl sulfone, alkyl sulfoxide, alkyl sulfite, sultone, sulfur dioxide, and sulfur trioxide. Examples of the latter include hydroquinone, catechol, and derivatives of these substances.

<Preparation of Composition>

The composition of the present disclosure can be prepared by using the components described above. The preparation devices and conditions are not particularly limited. For example, the composition can be prepared by subjecting the acrylamide compound represented by general formula (1) above, a multifunctional monomer, a polymerization initiator, a pigment, a dispersant, etc., to a dispersion treatment using a dispersing is machine such as a ball mill, a kitty mill, a disk mill, a pin mill, and a DYNO-MILL to prepare a pigment liquid dispersion, and further mixing the pigment liquid dispersion with a polymerization inhibitor and a surfactant.

<Viscosity>

The viscosity of the composition of the present disclosure has no particular limit because it can be adjusted depending on the purpose and application devices. For example, if an ejecting device that ejects the composition from nozzles is employed, the viscosity thereof is preferably in the range of 3 mPa·s to 40 mPa·s, more preferably 5 mPa·s to 15 mPa·s, and particularly preferably 6 mPa·s to 12 mPa·s in the temperature range of 20 degrees C. to 65 degrees C., preferably at 25 degrees C. In addition, it is particularly preferable to satisfy this viscosity range by the composition free of the organic solvent described above. Incidentally, the viscosity can be measured by a cone plate rotary viscometer (VISCOMETER TVE-22L, manufactured by TOKI SANGYO CO., LTD.) using a cone rotor (1° 34'×R24) at a number of rotation of 50 rpm with a setting of the temperature of hemathermal circulating water in the range of 20 degrees C. to 65 degrees C. VISCOMATE VM-150III can be used for the temperature adjustment of the circulating water.

<Curing Unit>

Examples of a curing unit configured to cure the composition of the present disclosure include thermal curing or curing by active energy rays. Of these units, curing by active energy rays is preferable.

Active energy rays used for curing the composition of the present disclosure are not particularly limited, so long as they are able to give necessary energy for allowing polymerization reaction of polymerizable components in the composition to proceed. Examples of the active energy rays include electron beams, $\alpha$-rays, $\beta$-rays, $\gamma$-rays, and X-rays, in addition to ultraviolet rays. When a light source having a particularly high energy is used, polymerization reaction can be allowed to proceed without a polymerization initiator. In addition, in the case of irradiation with ultraviolet ray, mercury-free is preferred in terms of protection of environment. Therefore, replacement with GaN-based semiconductor ultraviolet light-emitting devices is preferred from industrial and environmental point of view. Furthermore, ultraviolet light-emitting diode (UV-LED) and ultraviolet laser diode (UV-LD) are preferable as an ultraviolet light source. Small sizes, long time working life, high efficiency, and high cost performance make such irradiation sources desirable.

Above all, in terms of energy saving and device downsizing, ultraviolet rays emitted by an ultraviolet light-emitting diode (hereinafter, may also be referred to as UV-LED) and having a peak in a wavelength range of 285 nm or greater but 405 nm or less (preferably, 365 nm or greater but 405 nm or less) are preferable. Generally, the light absorption spectrum of polymerization initiators is broad, and use of UV-LED configured to emit a narrow specific wavelength range makes it difficult to improve the curability of compositions. Hence, use of the composition of the present disclosure excellent in curability even if UV-LED is used is preferable.

<Application Field>

The application field of the composition of the present disclosure is not particularly limited. It can be applied to any field where active-energy-ray-curable compositions are used. For example, the composition is selected to a particular application and used for a resin for processing, a paint, an adhesive, an insulant, a releasing agent, a coating material, a sealing material, various resists, and various optical materials.

Furthermore, the composition of the present disclosure can be used to form two-dimensional texts, images, and designed coating film on various substrates and in addition used as a solid object forming material to form a three-dimensional object. This three dimensional object forming material may also be used as a binder for powder particles used in a powder layer laminating method of forming a three-dimensional object by repeating curing and layer-forming of powder layers, and as a three-dimensional object constituent material (a model material) and a supporting member used in an additive manufacturing method (a stereolithography method) as illustrated in FIG. 1 and FIGS. 2A to 2D. FIG. 1 is a diagram illustrating a method of additive manufacturing (to be described in detail below) to sequentially form layers of the composition of the present disclosure one on top of the other by repeating discharging the composition to particular areas followed by curing upon irradiation of an active energy ray. FIGS. 2A to 2D are each a diagram illustrating a method of additive manufacturing to sequentially form cured layers 6 having respective predetermined forms one on top of the other on a movable stage 3 by irradiating a storing pool (storing part) 1 of the composition 5 of the present disclosure with the active energy ray 4.

An apparatus for fabricating a three-dimensional object by the composition of the present disclosure is not particularly limited and can be a known apparatus. For example, the apparatus includes a containing device, a supplying device, and a discharging device of the composition, and an active energy ray irradiator.

In addition, the present disclosure includes cured materials obtained by curing the composition and processed products obtained by processing structures having the cured materials on a substrate. The processed product is fabricated by, for example, heat-drawing and punching a cured material or structure having a sheet-like form or film-like form. Examples thereof are gauges or operation panels of vehicles, office machines, electric and electronic machines, and cameras.

The substrate is not particularly limited. It can suitably be selected to a particular application. Examples thereof include paper, thread, fiber, fabrics, leather, metal, plastic, glass, wood, ceramic, or composite materials thereof. Of these, plastic substrates are preferred in terms of processability.

Moreover, the composition of the present disclosure not only forms two-dimensional texts, images, and designed coating film on various substrates, but also, for example, a cured product obtained by curing the composition and an artificial nail formed by processing a structure having the cured product over a nail or a nail-shaped plastic base material. The composition of the present disclosure is particularly suitable as a base coat for an artificial nail composition, because the composition is excellent in removability and close adhesiveness with nails.

(Artificial Nail Composition, Nail Decoration Material, and Artificial Nail)

An artificial nail composition of the present disclosure contains the composition of the present disclosure and further contains other components as needed.

Additives such as a colorant (e.g., a pigment and a dye), an inorganic filler (e.g., metal powder, calcium carbonate, talc, silica, alumina, and aluminum hydroxide), a flame retardant, an organic filler, an antioxidant, a polymerization inhibitor, a defoaming agent, a coupling agent, a leveling agent, and a rheology control agent may be blended in an appropriate amount in the artificial nail composition of the present disclosure so long as the features of the present disclosure are not spoiled.

Examples of the nail decoration material include manicures, pedicures, sculptures, and gel nails used for decoration or reinforcement of nails.

Examples of the artificial nail include a fake nail formed of a synthetic resin over a nail (real nail).

The artificial nail composition of the present disclosure is a composition to be coated over a nail of a human or an animal or over any other artificial nail and cured by light exposure, to form an artificial nail. The artificial nail formed of the artificial nail composition of the present disclosure can be removed by a removing method using, for example, an organic solvent.

An artificial nail of the present disclosure refers to a layer formed over a nail of a human or an animal or over any other artificial nail with a view to decoration or protection, or both thereof. Further, examples of the any other artificial nail include an arbitrary-shaped resin base material (fake nail) for nail decoration or protection, or both thereof.

Note that "a nail of a human and an animal, and any other artificial nail" will also be referred to simply as "a nail".

The shape of the artificial nail is not particularly limited and may be a desired shape. For example, the artificial nail may be formed in a manner to coat the surface of a nail or may be formed over a part of a nail, or with the use of, for example, a nail form, may be formed in a shape larger than a nail for nail extension.

The thickness of the artificial nail composition of the present disclosure can be controlled by coating. The thickness of the entire artificial nail is not particularly limited so long as the thickness is in a range of typical thicknesses of artificial nails, and is preferably in a range of 10 micrometers or greater but 2,000 micrometers or less in terms of durability and removability.

For example, it is common that the configuration of an artificial nail is a layer structure including any one or more selected from, for example, in order of closeness to a nail, a primer layer (a layer between the nail and a base layer for improving an adhesive force with the nail when the adhesive force is insufficient only with the base layer), a base layer (a layer between the nail and a color layer for improving the adhesive force and preventing color migration to the nail), a color layer (a layer containing a colorant), and a top layer (an outermost layer for improving durability, gloss, and aesthetic appearance). The artificial nail composition of the present disclosure can be suitably used for any of a base layer or a color layer or a top layer, or all thereof.

Above all, in view of durability and removability, it is preferable that a layer obtained by curing the artificial nail composition of the present disclosure be in contact with a nail.

Moreover, separately, a primer layer or a base layer or a color layer or a top layer, or all thereof may be provided as an upper layer of an artificial nail layer formed of the artificial nail composition of the present disclosure (the upper layer being a surface at a side of the artificial nail layer opposite to the nail) or as a lower layer (a surface between the artificial nail layer and the nail) with a view to imparting a color or gloss or close adhesiveness, or all thereof.

The artificial nail composition of the present disclosure is a photocurable artificial nail composition (also referred to as "artificial nail composition for gel nail") as a nail decoration material, and is an artificial nail composition curable by active energy rays.

<Stored Container>

The stored container of the present disclosure contains the composition and is suitable for the applications as described above. For example, a container that stores the composition of the present disclosure can be used as a composition cartridge or a composition bottle. Therefore, users can avoid direct contact with the composition during operations such as transfer or replacement of the composition, so that fingers and clothes are prevented from contamination. Furthermore, inclusion of foreign matters such as dust in the composition can be prevented. In addition, the container can be of any size, any form, and any material. For example, is the container can be designed to a particular application. It is preferable to use a light blocking material to block the light or cover a container with a light blocking sheet, etc.

<<Image Forming Method and Forming Apparatus>>

In an image forming method of the present disclosure, a step of applying the composition of the present disclosure is not particularly limited, and examples include a coating tool such as a brush and a method for discharging the composition of the present disclosure. Examples of a curing step include active energy rays and heating. In order to cure the composition of the present disclosure with active energy rays, an irradiating step of irradiating the composition with active energy rays may be provided, an image forming apparatus of the present disclosure may include an irradiating unit configured to irradiate the composition with active energy rays and a storing part configured to store the composition of the present disclosure, and the container may be accommodated in the storing part. Further, a step of coating the composition of the present disclosure with a coating tool such as a brush and a coating unit, and a discharging step of discharging the composition of the present disclosure and a discharging unit may be provided. The discharging method is not particularly limited and examples of the discharging method include a continuous jetting method and an on-demand method. Examples of the on-demand method include a piezo is method, a thermal method, and an electrostatic method.

FIG. 1 is a schematic diagram illustrating another example of the image forming apparatus (apparatus to fabricate a 3D object) of the present disclosure. An image forming apparatus 39 illustrated in FIG. 1 sequentially forms thin layers one on top of the other using a head unit having inkjet heads arranged movable in the directions indicated by the arrows A and B. In the image forming apparatus 39, an ejection head unit 30 for additive manufacturing ejects a first composition, and ejection head units 31 and 32 for support and curing these compositions eject a second composition having a different composition from the first composition, while ultraviolet irradiators 33 and 34 adjacent to the ejection head units 31 and 32 cure the compositions. To be more specific, for example, after the ejection head units 31 and 32 for support eject the second composition onto a substrate 37 for additive manufacturing and the second composition is solidified by irradiation of an active energy ray to form a first substrate layer having a pool for composition, the ejection head unit 30 for additive manufacturing ejects the first composition onto the pool followed by irradiation of an active energy ray for solidification, thereby forming a first additive manufacturing layer. This step is repeated multiple times lowering the stage 38 movable in the vertical direction to laminate the supporting layer and the additive manufacturing layer to fabricate a solid object 35. Thereafter, an additive manufacturing support 36 is removed, if desired. Although only a single ejection head unit 30 for additive manufacturing is provided to the image forming apparatus illustrated 39 in FIG. 1, it can have two or more units 30. Further, a hand or a finger may be put over the substrate 37 for additive manufacturing to form an image over a nail.

EXAMPLES

The present disclosure will be described below by way of Examples. The present disclosure should not be construed as being limited to these Examples.

Names of compounds used for composition preparation, manufacturer names, and product names are presented in Table 1. Monomers, which were acrylamide compounds, were synthesized in the manners described in Synthesis examples 1 to 5. Identification of the synthesized compounds was performed by a nuclear magnetic resonance spectroscopy method (instrument used: "JNM-ECX500" available from JEOL Ltd.), and purity measurement was performed by a gas chromatograph method (instrument used: "GCMS-QP2010 PLUS" available from Shimadzu Corporation). These chemical analyses were performed according to the rule.

TABLE 1

| | Abbrev. | Name or structure of compound | Synthesis method, or manufacturer name and product name |
|---|---|---|---|
| Acrylamide compound represented by general formula (1) | A1-1 | 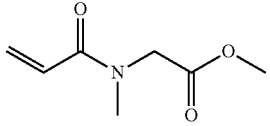 | (see Synthesis example 1) |
| | A1-2 | 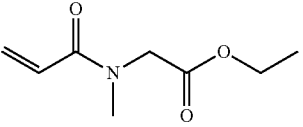 | (see Synthesis example 2) |
| | A1-3 | 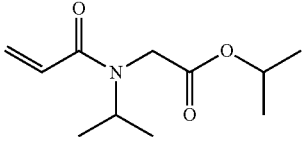 | (see Synthesis example 3) |
| | A1-4 | 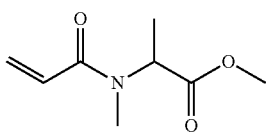 | (see Synthesis example 4) |
| Polymerizable compound other than general formula (1) | A2-1 | 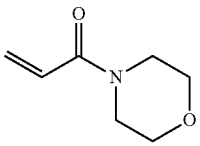 | Acryloylmorpholine available from KJ Chemicals Corporation |
| | A2-2 | 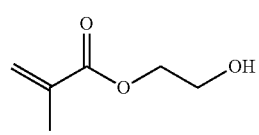 | 2-Hydroxyethyl methacrylate available from Tokyo Chemical Industry Co., Ltd. |
| Multifunctional monomer | B-1 | Structure for B-1 is provided after table | Caprolactone-modified pentaerythritol hexaacrylate (DPCA-60) available from Nippon Kayaku Co., Ltd. |
| | B-2 | 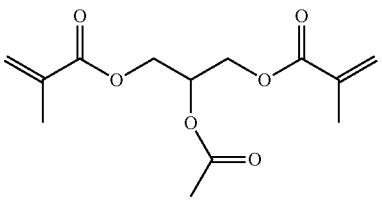 [SMILES: C=C(C)C(=O)OCC(COC(=O)C(=C)C)OC(C)=O] | (see Synthesis example 5) |
| | B-3 | 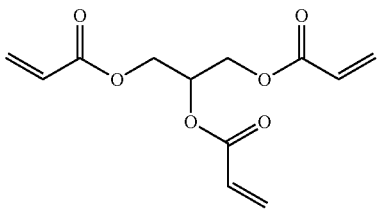 [SMILES: C=CC(=O)OCC(COC(=O)C=C)OC(=O)C=C] | Glycerin triacrylate M-3547 available from Toagosei Co., Ltd. |

TABLE 1-continued

| Abbrev. | | Name or structure of compound | Synthesis method, or manufacturer name and product name |
|---|---|---|---|
| | B-4 | (structure shown) | Pentaerythritol tetraacrylate A-TMMT available from Shin-Nakamura Chemical Co., Ltd. |
| Polymerization initiator | C-1 | Bis(2,4,5-trimethyl benzoyl)phenyl) phosphine oxide | IRGACURE 819 available from BASF Japan Ltd. |
| | C-2 | 2-Methyl-1-(4-methyl-thiophenyl)-2-morpholinopropan-1-one | IRGACURE 907 available from BASF Japan Ltd. |

[Synthesis example 1]

Structure for multifunctional monomer B-1

Synthesis of N-Acryloyl-N-Methyl Glycine Methyl Ester (A1-1)

N-methyl glycine methyl ester hydrochloride salt (available from Sigma-Aldrich Japan, reagent) (0.30 moles), potassium carbonate (available from Kanto Chemical Co., Inc., reagent) (0.45 moles), and water (400 mL) were stirred and mixed at from 0 degrees C. through 10 degrees C., and with that temperature maintained, acrylic acid chloride (available from Wako Pure Chemical Industries, Ltd., reagent) (0.33 moles) was slowly dropped to the resultant. After dropping was completed, the resultant was subjected to extraction three times with ethyl acetate (available from Kanto Chemical Co., Inc., reagent) (400 mL), and together with the ethyl acetate layer, the resultant was washed once with water (400 mL). Ethyl acetate was evaporated at a reduced pressure at 40 degrees C., to obtain the intended N-acryloyl-N-methyl glycine methyl ester (A1-1) (0.20 moles) in the form of an almost colorless, transparent is liquid. The purity was 98.3% by mass.

N-acryloyl-N-methyl glycine methyl ester (A1-1) has a molecular weight of 157.2, and is a publicly known compound (CAS registration No. 72065-23-7).

Synthesis Example 2

Synthesis of N-Acryloyl-N-Methyl Glycine Ethyl Ester (A1-2)

An intended N-acryloyl-N-methyl glycine ethyl ester (A1-2) (0.22 moles) was obtained in the form of an almost colorless, transparent liquid in the same manner as in Synthesis example 1, except that unlike in Synthesis example 1, N-methyl glycine methyl ester hydrochloride salt was changed to N-methyl glycine ethyl ester hydrochloride salt (available from Tokyo Chemical Industry Co., Ltd., reagent). The purity was 98.5% by mass.

N-acryloyl-N-methyl glycine ethyl ester (A1-2) has a molecular weight of 171.2, and is a publicly known compound (CAS registration No. 170116-05-9).

Synthesis Example 3

Synthesis of N-Acryloyl-N-Isopropyl Glycine Isopropyl Ester (A1-3)

An intended N-acryloyl-N-isopropyl glycine isopropyl ester (A1-3) (0.22 moles) was obtained in the form of an almost colorless, transparent liquid in the same manner as in Synthesis example 1, except that unlike in Synthesis example 1, N-methyl glycine methyl ester hydrochloride salt was changed to N-isopropyl glycine isopropyl ester hydrochloride salt (available from Tokyo Chemical Industry Co., Ltd., reagent). The purity was 98.5% by mass.

N-acryloyl-N-isopropyl glycine isopropyl ester (A1-3) had a molecular weight of 213.3.

Synthesis Example 4

Synthesis of N-Acryloyl-N-Methyl Alanine Methyl Ester (A1-4)

An intended N-acryloyl-N-methyl alanine methyl ester (A1-4) (0.22 moles) was obtained in the form of an almost colorless, transparent liquid in the same manner as in Synthesis example 1, except that unlike in Synthesis example 1, N-methyl glycine methyl ester hydrochloride salt was changed to N-methyl alanine methyl ester hydrochloride salt (available from Tokyo Chemical Industry Co., Ltd., reagent). The purity was 98.5% by mass.

N-acryloyl-N-methyl alanine methyl ester (A1-4) had a molecular weight of 171.2.

Synthesis Example 5

Glycerol dimethacrylate (5.7 g) (25 mmol) available from Tokyo Chemical Industry Co., Ltd. was added in dehydrated dichloromethane (100 mL). After a flask was internally purged with an argon gas, triethyl amine (3.6 g) (36 mmol) was added. Next, after the resultant was cooled to about −10 degrees C., acetic acid chloride (2.4 g) (30 mmol) was slowly dropped to adjust the temperature in the system to from −10 degrees C. through −5 degrees C., followed by stirring at room temperature (25 degrees C.) for 2 hours. Further, after a precipitate was removed by filtration, the filtrate was washed with water, a saturated sodium bicarbonate aqueous solution, and a saturated sodium chloride aqueous solution, followed by drying with sodium sulfate and concentration at a reduced pressure, to obtain a yellow oily matter. Further, the yellow oily matter was refined by column chromatography in which the column was filled with WAKOGEL C300 (available from Wako Pure Chemical Industries, Ltd.) (200 g) and hexane and ethyl acetate were used as eluates, to obtain a colorless oily matter (3.2 g) (at a yield of about 47%) of a compound (B-2) represented by a structural formula below.

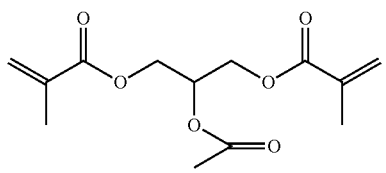 [SMILES: C=C(C)C(=O)OCC(COC(=O)C(=C)C)OC(C)=O]

The identification data is as presented below.
$^1$H-NMR (CDCl3): δ1.95 (s, 6H), 2.09 (d, 3H), 4.23-4.42 (m, 4H), 5.35-5.42 (m, 1H), 5.59-5.63 (m, 2H), 6.10-6.15 (m, 2H)

Examples 1 to 11 and Comparative Examples 1 to 7

Production of Composition

The components presented in Table 2 and Table 3 were mixed uniformly and filtrated through a membrane filter to remove coarse particles, to produce the compositions of Examples 1 to 11 and Comparative Examples 1 to 7.

TABLE 3

| | Abbreviation | Comp. Ex. | | | | | | |
| --- | --- | --- | --- | --- | --- | --- | --- | --- |
| | | 1 | 2 | 3 | 4 | 5 | 6 | 7 |
| Acrylamide compound (A1) | A1-1 | 60 | | | | | | 50 |
| | A1-2 | | 15 | | | | | |
| | A1-3 | | | 60 | | | | |
| | A1-4 | | | | 60 | | | |
| Polymerizable compound other than (A1) | A2-1 | | | | | 45 | | |
| | A2-2 | | | | | | 45 | |
| Multifunctional monomer | B-1 | 30 | | | | | | 50 |
| | B-2 | | 75 | | | 45 | 45 | |
| | B-3 | | | 30 | | | | |
| | B-4 | | | | 30 | | | |
| Polymerization initiator | C-1 | | | | | | | |
| | C-2 | 10 | 10 | 10 | 10 | 10 | 10 | |
| Total (% by mass) | | 100 | 100 | 100 | 100 | 100 | 100 | 100 |

<Curability>

Each composition was coated over a polyethylene terephthalate PET) film to have a thickness of 10 micrometers, and irradiated with an irradiation energy of 600 mJ/cm$^2$ per pass by a metal halide lamp under the atmosphere, to produce a cured product and evaluate curability according to the criteria described below based on finger touch by the tip of a finger. The results are presented in Table 4 and Table 5.
[Evaluation Criteria]
  A: No tack was felt.
  B: Tack was felt.
  C: The composition did not cure.
<Durability>
A test piece of a cured product produced in the same manner as producing the cured product in the evaluation of the curability was immersed in purified water at from 20 degrees C. through 25 degrees C. for 5 hours, to visually observe presence or absence of peeling and dissolution of the cured product and evaluate durability according to the criteria described below. The results are presented in Table 4 and Table 5.
[Evaluation Criteria]
  A: No peeling and dissolution were observed.
  B: Peeling or dissolution was observed.
<Evaluation of Odor>
Odor of each composition was confirmed according to the procedures (1) to (3) below, to evaluate "degree of odor-

TABLE 2

| | Abbreviation | Ex. | | | | | | | | | | |
| --- | --- | --- | --- | --- | --- | --- | --- | --- | --- | --- | --- | --- |
| | | 1 | 2 | 3 | 4 | 5 | 6 | 7 | 8 | 9 | 10 | 11 |
| Acrylamide compound (A1) | A1-1 | 23 | 45 | 45 | 45 | 45 | 45 | 48 | 40 | | | |
| | A1-2 | | | | | | | | | 45 | | |
| | A1-3 | | | | | | | | | | 45 | |
| | A1-4 | | | | | | | | | | | 45 |
| Polymerizable compound other than (A1) | A2-1 | | | | | | | | | | | |
| | A2-2 | | | | | | | | | | | |
| Multifunctional monomer | B-1 | 67 | 45 | | | | 45 | 49 | 40 | 45 | 45 | 45 |
| | B-2 | | | 45 | | | | | | | | |
| | B-3 | | | | 45 | | | | | | | |
| | B-4 | | | | | 45 | | | | | | |
| Polymerization initiator | C-1 | | | | | | 10 | | | | | |
| | C-2 | 10 | 10 | 10 | 10 | 10 | | 3 | 20 | 10 | 10 | 10 |
| Total (% by mass) | | 100 | 100 | 100 | 100 | 100 | 100 | 100 | 100 | 100 | 100 | 100 | lessness" according to the evaluation criteria described below. The results are presented in Table 4 and Table 5.

(1) Each composition was weighed out in an amount of about 100 mg (0.1 g) in a 50 mL sample bottle (glass bottle), and capped.

(2) The resultant was left to stand at room temperature (25 degrees C.) for 30 minutes.

(3) The nose was brought close to the sample bottle (glass bottle) to smell any odor when the bottle was uncapped.

[Evaluation Criteria]

A: No odor was felt, or an odor, if felt, was not uncomfortable.

B: A characteristic odor caused a feeling of discomfort.

C: A characteristic odor caused a strong feeling of discomfort.

TABLE 4

| | Ex. | | | | | | | | | | |
|---|---|---|---|---|---|---|---|---|---|---|---|
| | 1 | 2 | 3 | 4 | 5 | 6 | 7 | 8 | 9 | 10 | 11 |
| Curability | A | A | A | A | A | A | A | A | A | A | A |
| Durability | A | A | A | A | A | A | A | A | A | A | A |
| Odor | A | A | A | A | A | A | A | A | A | A | A |

TABLE 5

| | Comp. Ex. | | | | | | |
|---|---|---|---|---|---|---|---|
| | 1 | 2 | 3 | 5 | 4 | 5 | 6 | 7 |
| Curability | A | B | A | A | A | A | A | C |
| Durability | B | A | B | B | B | B | B | — |
| Odor | A | A | A | A | A | A | B | A |

*In Table 5, the sign "—" in the durability section of Comparative Example 7 means that the durability was unmeasurable.

From the results of Table 4 and Table 5, the compositions of Examples 1 to 11 were superior to the compositions of Comparative Examples 1 to 7 in curability, durability and odorlessness, and would be suitably applicable as an artificial nail composition in particular.

Aspects of the present disclosure are, for example, as follows.

<1> A composition including:
an acrylamide compound represented by general formula (1) below in an amount of 20% by mass or greater but 50% by mass or less;
a multifunctional monomer in an amount of 40% by mass or greater but 70% by mass or less; and
a polymerization initiator,

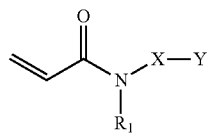

General formula (1)

where in general formula (1), $R_1$ represents an alkyl group containing 1 through 6 carbon atoms, X represents an alkylene group containing 1 through 6 carbon atoms, and Y represents any one selected from the group consisting of general formula (2) below and general formula (3) below,

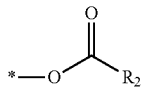

General formula (2)

where in general formula (2), $R_2$ represents an alkyl group containing 1 through 10 carbon atoms, and * represents a binding site with X above,

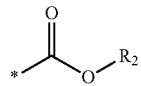

General formula (3)

where in general formula (3), $R_2$ represents an alkyl group containing 1 through 10 carbon atoms, and * represents a binding site with X above.

<2> The composition according to <1>, including;
the acrylamide compound represented by the general formula (1) in an amount of 23% by mass or greater but 45% by mass or less;
the multifunctional monomer in an amount of 45% by mass or greater but 67% by mass or less; and
the polymerization initiator.

<3> The composition according to <1> or <2>,
wherein Y in the general formula (1) representing the acrylamide
compound is the general formula (3), and
wherein $R_2$ in the general formula (3) is an alkyl group containing 1 through 2 carbon atoms.

<4> The composition according to any one of <1> to <3>, wherein the multifunctional monomer is a multifunctional monomer that is bifunctional or greater but hexafunctional or less.

<5> The composition according to any one of <1> to <4>, wherein a content of the polymerization initiator is 1% by mass or greater but 20% by mass or less.

<6> The composition according to any one of <1> to <5>, wherein the composition is free of an organic solvent.

<7> The composition according to any one of <1> to <6>, wherein the composition is an active-energy-ray-curable composition.

<8> A stored container including:
the composition according to any one of <1> to <7>; and
a container,
wherein the composition is stored in the container.

<9> A two-dimensional or three-dimensional image forming apparatus including:
a storing part configured to store the composition according to any one of <1> to <7>;
an applying unit configured to apply the composition; and
a curing unit configured to cure the composition.

<10> The image forming apparatus according to <9>, wherein the curing unit is a UV-LED configured to emit an ultraviolet ray having a peak in a wavelength range of 365 nm or greater but 405 nm or less.

<11> A two-dimensional or three-dimensional image forming method including:
applying the composition according to any one of <1> to <7>; and
curing the composition.

<12> The image forming method according to <11>, wherein the curing includes irradiating the composition with an ultraviolet ray having a peak in a wavelength range of 365 nm or greater but 405 nm or less by a UV-LED.
<13> An artificial nail composition including the composition according to any one of <1> to <7>.
<14> A nail decoration material including the artificial nail composition according to <13>.
<15> An artificial nail including a cured product of the artificial nail composition according to <13>.

The composition according to any one of <1> to <7>, the stored container according to <8>, the two-dimensional or three-dimensional image forming apparatus according to <9> or <10>, the two-dimensional or three-dimensional image forming method according to <11> or <12>, the artificial nail composition according to <13>, the nail decoration material according to <14>, and the artificial nail according to <15> can solve the various problems in the related art and can achieve the object of the present disclosure.

What is claimed is:

1. A composition comprising:
an acrylamide compound of formula (I) in an amount of 23% by mass or greater but 45% by mass or less;
a multifunctional monomer in an amount of 45% by mass or greater but 67% by mas or less; and
a radical polymerization initiator,

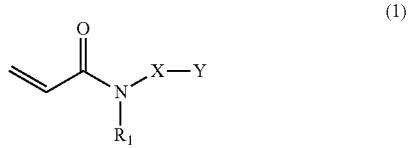

(1)

wherein R₁ represents an alkyl group that comprises 1 through 6 carbon atoms, X represents an alkylene group that comprises 1 through 6 carbon atoms, and Y represents formula (3),

(3)

wherein, R₂ represents an alkyl group that comprises 1 through 10 carbon atoms, and * represents a biding site with X above; and
wherein
the multifunctional monomer is at least bifunctional and at most hexafunctional, and the mass % content of the multifunctional monomer is greater than or equal to the mass % content of the acrylamide compound of formula (I).

2. The composition according to claim 1,
the amount of the acrylamide compound of formula (1) is 23% by mass or greater but 45% by mass or less; and
the amount of the multifunctional monomer is 45% by mass or greater but 67% by mass or less.

3. The composition according to claim 1,
wherein Y is of formula (3), and
wherein R₂ is an alkyl group that comprises 1 through 2 carbon atoms.

4. The composition according to claim 1,
wherein the multifunctional monomer comprises a multifunctional monomer that is bifunctional or greater but hexafunctional or less.

5. The composition according to claim 1,
wherein a content of the radical polymerization initiator is 1% by mass or greater but 20% by mass or less.

6. The composition according to claim 1,
wherein the composition is an active-energy-ray-curable composition.

7. A stored container comprising:
the composition according to claim 1; and
a container,
wherein the composition is stored in the container.

8. An artificial nail composition comprising the composition according to claim 1.

9. A nail decoration material comprising the artificial nail composition according to claim 8.

10. An artificial nail comprising a cured product of the artificial nail composition according to claim 8.

11. A two-dimensional or three-dimensional image forming apparatus comprising:
a storing part configured to store a composition;
an applying unit configured to apply the composition; and
a curing unit configured to cure the composition.
wherein the composition comprises:
an acrylamide compound of formula (I) in an amount of 23% by mass or greater but 45% by mass or less;
a multifunctional monomer in an amount of 45% by mass or greater but 67 by mass or less; and
a radical polymerization initiator,

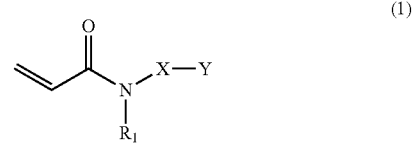

(1)

wherein R₁ represents an alkyl group that comprises 1 through 6 carbon atoms, X represents an alkylene group that comprises 1 through 6 carbon atoms, and Y represents formula (3),

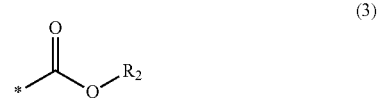

(3)

wherein, R₂ represents an alkyl group that comprises 1 through 10 carbon atoms, and * represents a biding site with X above; and
wherein
the multifunctional monomer is at least bifunctional and at most hexafunctional, and the mass % content of the multifunctional monomer is greater than or equal to the mass % content of the acrylamide compound of formula (I).

12. A two-dimensional or three-dimensional image forming method comprising:
applying a composition: and
curing the composition,
wherein the composition comprises:
an acrylamide compound of formula (I) in an amount of 23% by mass or greater but 45% by mass or less;

a multifunctional monomer in an amount of 45% by mass or greater but 67% by mass or less; and
a radical polymerization initiator,

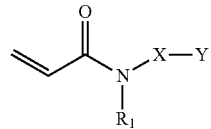

(1)

wherein $R_1$ represents an alkyl group that comprises 1 through 6 carbon atoms, X represents an alkylene group that comprises 1 through 6 carbon atoms, and Y represents formula (3),

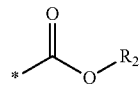

(3)

wherein, $R_2$ represents an alkyl group that comprises 1 through 10 carbon atoms, and * represents a biding site with X above; and
wherein
the multifunctional monomer is at least bifunctional and at most hexafunctional, and the mass % content of the multifunctional monomer is greater than or equal to the mass % content of the acrylamide compound of formula (I).

* * * * *